US011989652B2

(12) United States Patent
Khosousi et al.

(10) Patent No.: US 11,989,652 B2
(45) Date of Patent: May 21, 2024

(54) METHODS AND SYSTEMS TO CONFIGURE AND USE NEURAL NETWORKS IN CHARACTERIZING PHYSIOLOGICAL SYSTEMS

(71) Applicant: Analytics For Life Inc., Toronto (CA)

(72) Inventors: Ali Khosousi, Toronto (CA); Timothy William Fawcett Burton, Toronto (CA); Horace R. Gillins, Toronto (CA); Shyamlal Ramchandani, Kingston (CA); William Sanders, Bethesda, MD (US); Ian Shadforth, Morrisville, NC (US)

(73) Assignee: Analytics For Life Inc., Toronto (CA)

( * ) Notice: Subject to any disclaimer, the term of this patent is extended or adjusted under 35 U.S.C. 154(b) by 0 days.

(21) Appl. No.: 18/114,753

(22) Filed: Feb. 27, 2023

(65) Prior Publication Data

US 2023/0289595 A1    Sep. 14, 2023

Related U.S. Application Data

(63) Continuation of application No. 16/725,430, filed on Dec. 23, 2019, now Pat. No. 11,589,829.

(Continued)

(51) Int. Cl.
    *G06V 10/00* (2022.01)
    *A61B 5/00* (2006.01)
    (Continued)

(52) U.S. Cl.
    CPC ............ *G06N 3/08* (2013.01); *A61B 5/7275* (2013.01); *G06F 18/214* (2023.01);
    (Continued)

(58) Field of Classification Search
    CPC ... A61B 5/7246; A61B 5/7267; A61B 5/0245; A61B 5/318; G06N 3/08; G06N 20/00;
    (Continued)

(56) References Cited

U.S. PATENT DOCUMENTS 8,923,958 B2    12/2014    Gupta et al.
9,289,150 B1     3/2016    Gupta et al.
(Continued)

FOREIGN PATENT DOCUMENTS

CN    107822622    3/2018
EP     2392262    12/2011
(Continued)

OTHER PUBLICATIONS

W. Liu et al., "Real-Time Multilead Convolutional Neural Network for Myocardial Infarction Detection," in IEEE Journal of Biomedical and Health Informatics, vol. 22, No. 5, pp. 1434-1444, Sep. 2018.*

(Continued)

*Primary Examiner* — Li Liu
(74) *Attorney, Agent, or Firm* — Meunier Carlin & Curfman LLC

(57) ABSTRACT

The exemplified methods and systems facilitate the configuration and training of a neural network (e.g., a deep neural network, a convolutional neural network (CNN), etc.), or ensemble(s) thereof, with a biophysical signal data set to ascertain estimate for the presence or non-presence of disease or pathology in a subject as well as to assess and/or classify disease or pathology, including for example in some cases the severity of such disease or pathology, in a subject. In the context of the heart, the methods and systems described herein facilitate the configuration and training of a neural network, or ensemble(s) thereof, with a cardiac signal data set to ascertain estimate for the presence or (Continued)

non-presence of coronary artery disease or coronary pathology.

14 Claims, 13 Drawing Sheets

Related U.S. Application Data

(60) Provisional application No. 62/907,141, filed on Sep. 27, 2019, provisional application No. 62/784,925, filed on Dec. 26, 2018.

(51) Int. Cl.
*G06F 18/21* (2023.01)
*G06F 18/214* (2023.01)
*G06N 3/08* (2023.01)
*G06N 20/00* (2019.01)
*G06V 10/776* (2022.01)

(52) U.S. Cl.
CPC ........... *G06F 18/217* (2023.01); *G06N 20/00* (2019.01); *G06V 10/776* (2022.01)

(58) Field of Classification Search
CPC ...... G06N 3/0454; G16H 50/20; G16H 50/30; G06K 9/6256; G06K 9/6262; G06T 2207/20081; G06T 2207/20084; G06T 2207/30048
See application file for complete search history.

(56) References Cited

U.S. PATENT DOCUMENTS

| | | | |
|---|---|---|---|
| 9,408,543 | B1 | 8/2016 | Gupta et al. |
| 9,597,021 | B1 | 3/2017 | Gupta et al. |
| 9,655,536 | B2 | 5/2017 | Gupta et al. |
| 9,737,229 | B1 | 8/2017 | Gupta et al. |
| 9,910,964 | B2 | 3/2018 | Burton et al. |
| 9,955,883 | B2 | 5/2018 | Gupta et al. |
| 9,968,265 | B2 | 5/2018 | Burton et al. |
| 10,039,468 | B2 | 8/2018 | Gupta et al. |
| 10,292,596 | B2 | 5/2019 | Shadforth et al. |
| 11,348,032 | B1 * | 5/2022 | Van Gael ............. G06F 8/31 |
| 2008/0103403 | A1 * | 5/2008 | Cohen ................. G16H 50/20 600/509 |
| 2013/0237870 | A1 | 9/2013 | Gregg et al. |
| 2014/0249424 | A1 | 9/2014 | Fan et al. |
| 2016/0361041 | A1 | 12/2016 | Barsimantov et al. |
| 2017/0119272 | A1 | 5/2017 | Gupta et al. |
| 2018/0000371 | A1 | 1/2018 | Gupta et al. |
| 2018/0078146 | A1 | 3/2018 | Shadforth et al. |
| 2018/0160917 | A1 * | 6/2018 | Liu ..................... A61B 5/7267 |
| 2018/0249960 | A1 | 9/2018 | Gupta et al. |
| 2019/0117164 | A1 | 4/2019 | Gupta et al. |
| 2019/0200893 | A1 | 7/2019 | Grouchy et al. |
| 2019/0214137 | A1 | 7/2019 | Gupta et al. |
| 2019/0365265 | A1 | 12/2019 | Grouchy et al. |
| 2019/0384757 | A1 | 12/2019 | Garrett et al. |
| 2020/0245889 | A1 | 8/2020 | Telenkov |

FOREIGN PATENT DOCUMENTS

| | | |
|---|---|---|
| EP | 2429644 | 3/2012 |
| KR | 10-2010-0128083 | 12/2010 |
| WO | 2016/207862 | 12/2016 |
| WO | 2017/033164 | 3/2017 |
| WO | 2017/062882 | 4/2017 |
| WO | 2017/212333 | 12/2017 |
| WO | 2017/221221 | 12/2017 |
| WO | 2018/055559 | 3/2018 |
| WO | 2018162957 | 9/2018 |

OTHER PUBLICATIONS

Bergstra, James, et al. "Algorithms for hyper-parameter optimization." Advances in neural information processing systems 24 (2011).*
Asadi, F., et al., "Cardiac Arrhythmia Recognition with Robust Discrete Wavelet-Based and Geometrical Feature Extraction via Classifiers of SVM and MLP-BP and PNN Neural Networks," Computing in Cardiology, Issue 43, 2015, pp. 933-936.
Bergstra, J., et al., "Random Search for Hyper-Parameter Optimization," Journal of Machine Learning Research, vol. 13, 2012, pp. 281-305.
Convolutional Neural Networks (CNNs/ConvNets), Stanford University course Cs231n: Convolutional Neural Networks for Visual Recognition, retrieved on Apr. 21, 2020 at https://cs231n.github.io/convolutional-networks/, 2015, 23 pages.
Ebrahimzadeh, E., et al., "A Novel Approach to Predict Sudden Cardiac Death (SCD) Using Nonlinear and Time-Frequency Analyses from HRV Signals," PloS One, vol. 9, Issue 2, e81896, 2014, 14 pages.
Itu, L., et al., "A machine-learning approach for computation of fractional flow reserve from coronary computed tomography," Journal of Applied Physiology, vol. 121, No. 1, 2016, pp. 42-52.
Neural Networks, introduction, Stanford University course CS231n: Convolutional Neural Networks for Visual Recognition, retrieved on Apr. 21, 2020 at http://cs231n.github.io/neural-networks-1/, 2015, 13 pages.
Pan, J., et al., "A Real-Time QRS Detection Algorithm," IEEE Transactions on Biomedical Engineering, vol. BME-32, No. 3, 1985, pp. 230-236.
Razzak, M.I., et al., "Deep Learning for Medical Image Processing: Overview, Challenges and Future," Classification in BioApps, retrieved from https://arxiv.org/ftp/arxiv/papers/1704/1704.06825.pdf, 2018, 30 pages.
Stratified ShuffleSplit cross-validator, scikit-learn 0.22.2, retrieved on Apr. 21, 2020 at http://scikitlearn.org/stable/modules/generated/sklearn.model_selection.StratifiedShuffleSplit.html, 2020, 2 pages.
International Search Report and Written Opinion, dated May 4, 2020, received in connection with corresponding International Patent Application No. PCT/IB2019/061314.
Avci, Anil, et al. "Association between the gensini score and carotid artery stenosis." Korean circulation journal 46.5 (2016): 639-645.
Liu, W., et al. "Real-Time Multilead Convolutional Neural Network for Myocardial Infarction Detection," IEEE Journal of Biomedical and Health Informatics, vol. 22, No. 5, 2018, pp. 1434-1444.
Supplementary Partial Search Report, dated Aug. 19, 2022, received in corresponding EP Patent Application No. 19901564.5.
The Extended European Search Report issued for Application No. 19901564.5, dated Nov. 21, 2022.

* cited by examiner

FIG. 6

METHODS AND SYSTEMS TO CONFIGURE AND USE NEURAL NETWORKS IN CHARACTERIZING PHYSIOLOGICAL SYSTEMS

RELATED APPLICATION

This U.S. patent application claims priority to, and the benefit of, U.S. Patent Provisional Application No. 62/784,925, filed Dec. 26, 2018, entitled "Method and System to Configure and Use Convolutional Neural Network to Assess Medical Disease," U.S. Patent Provisional Application No. 62/907,141, filed Sep. 27, 2019, entitled "Methods and Systems to Configure and Use Convolutional Neural Networks in Characterizing Physiological Systems," and U.S. Non-Provisional patent application Ser. No. 16/725,430, filed Dec. 23, 2019, entitled "Methods and Systems to Configure and Use Neural Networks in Characterizing Physiological Systems," each of which is incorporated by reference herein in its entirety.

FIELD OF THE INVENTION

The present disclosure generally relates to non-invasive methods and systems for characterizing cardiovascular and other physiological systems. More specifically, in an aspect, the present disclosure relates to non-invasive methods that utilize phase space data to generate phase space analysis data set/images from an acquired biophysical signal (e.g., a cardiac signal, a brain/neurological signal, signals associated with other biological systems, etc.) in particular, to be used in the prediction and localization of coronary artery stenosis of the myocardium and characterize myocardial ischemia, among other cardiac and non-cardiac disease and pathologies.

BACKGROUND

Ischemic heart disease, also known as cardiac ischemia or myocardial ischemia, is a disease or group of diseases characterized by a reduced blood supply to the heart muscle, usually due to coronary artery disease (CAD). CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmia. An arrhythmia is an abnormal heart rhythm and can include any change from the normal sequence of electrical conduction of the heart and in some cases can lead to cardiac arrest.

The evaluation of CAD can be complex, and many techniques and tools are used to assess the presence and severity of the condition. In the case of electrocardiography, a field of cardiology in which the heart's electrical activity is analyzed to obtain information about its structure and function, significant ischemic heart disease can alter ventricular conduction properties of the myocardium in the perfusion bed downstream of a coronary artery narrowing or occlusion. This pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

Machine learning techniques predict outcomes based on sets of input data. For example, machine learning techniques are being used to recognize patterns and images, supplement medical diagnoses, and so on. Machine learning techniques rely on a set of features generated using a training set of data (i.e., a data set of observations, in each of which an outcome to be predicted is known), each of which represents some measurable aspect of observed data, to generate and tune one or more predictive models. For example, observed signals (e.g., heartbeat signals from a number of subjects) may be analyzed to collect frequency, average values, and other statistical information about these signals. A machine learning technique may use these features to generate and tune a model that relates these features to one or more conditions, such as some form of cardiovascular disease (CVD), including coronary artery disease (CAD), and then apply that model to data sources with unknown outcomes, such as an undiagnosed patient or future patterns, and so on. Conventionally, in the context of cardiovascular disease, these features are manually selected from conventional electrocardiogram and combined by data scientists working with domain experts.

SUMMARY

The exemplified methods and systems described herein facilitate the configuration and training of a neural network (e.g., a deep neural network, a convolutional neural network (CNN), etc.), or ensemble(s) thereof, with a phase gradient biophysical signal data set (e.g., a wide-band phase gradient biophysical signal data set) to assess and/or classify disease in a subject. In the context of the heart, the methods and systems described herein facilitate the configuration and training of a neural network (e.g., a deep neural network, a convolutional neural network (CNN)), or ensemble(s) thereof, with a phase gradient cardiac signal data set (e.g., a wide-band phase gradient cardiac signal data set) to assess and/or classify coronary artery disease in a subject. Remarkably, the exemplary system in such embodiment has been shown to have diagnostic ability of assessing overall coronary artery disease in a patient with an AUC score of 0.61 or greater using a completely non-invasive method of measuring phase gradient biophysical signals from a person on a per-beat basis (also referred to herein as "beat-to-beat"). In some embodiments, the exemplary system is further configured to localize the presence of coronary artery disease in major coronary arteries (e.g., in the right coronary artery (RCA), left anterior descending (LAD) artery, and/or the left circumflex artery (LCX), among others). In some embodiments, the exemplary system is configured to generate and co-present phase-space analysis data sets/images along with the coronary artery disease assessment and localization. While discussed in the context of cardiac signal, the exemplified methods and systems described herein facilitate the configuration and training of a neural network (e.g., a deep neural network, a convolutional neural network (CNN), etc.), or ensemble(s) thereof, with other biophysical signal (e.g., neurological signal, pulmonary, etc.) to assess and/or classify disease in a subject or in specific anatomical structure or organs of the subject.

As used herein, the term "cardiac signal" refers to one or more signals associated with the structure, function and/or activity of the cardiovascular system—including aspects of that signal's electrical/electrochemical conduction—that, e.g., cause contraction of the myocardium. A cardiac signal may include, in some embodiments, electrocardiographic signals such as, e.g., those acquired via an electrocardiogram (ECG) or other modalities.

As used herein, the term "neurological signal" refers to one or more signals associated with the structure, function and/or activity of the central and peripheral nervous systems, including the brain, spinal cord, nerves, and their associated neurons and other structures, etc., and including aspects of that signal's electrical/electrochemical conduction. A neurological signal may include, in some embodiments, electroencephalographic signals such as, e.g., those acquired via an electroencephalogram (EEG) or other modalities.

A "biophysical signal" is not limited to a cardiac signal, a neurological signal, or a photoplethysmographic signal but encompasses any physiological signal from which information may be obtained. Not intending to be limited by example, one may classify biophysical signals into types or categories that can include, for example, electrical (e.g., certain cardiac and neurological system-related signals that can be observed, identified and/or quantified by techniques such as the measurement of voltage/potential, impedance, resistivity, conductivity, current, etc. in various domains such as time and/or frequency), magnetic, electromagnetic, optical (e.g. signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g. signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), an organ system (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements and their subatomic components. Unless stated otherwise, the term "biophysical signal acquisition" generally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light and other ways of actively interrogating the body tissue that does not involve ionizing energy or radiation (e.g., X-ray). Active biophysical signal acquisition may involve excitation-emission spectroscopy (including, e.g., excitation-emission fluorescence). Active biophysical signal acquisition may also involve transmitting ionizing energy or radiation (e.g., X-ray) (also referred to as "ionizing biophysical signal") to the body tissue. Passive and active biophysical signal acquisition means can be performed with conjunction with invasive procedures (e.g., via surgery or invasive radiologic intervention protocols) or non-invasively (e.g., via imaging).

A "photoplethysmographic signal(s)" as used herein refers to signal waveforms acquired from optical sensors that corresponds to measured changes in light absorption by oxygenated and deoxygenated hemoglobin, such as light having wavelengths in the red and infrared spectrum. Photoplethysmographic signal(s), in some embodiments, include raw signal(s) acquired via a pulse oximeter or a photoplethysmogram (PPG). In some embodiments, photoplethysmographic signal(s) are acquired from custom or dedicated equipment or circuitries (including off-the-shelf devices) that are configured to acquire such signal waveforms for the purpose of diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near infrared, blue and green may be used in different combinations, depending on the type and/or mode of PPG being employed.

The methods and systems described in the various embodiments herein are not so limited and may be utilized in any context of another physiological system or systems, organs, tissue, cells, etc. of a living body. By way of example only, two biophysical signal types that may be useful in the cardiovascular context include cardiac signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography.

In the context of the present disclosure, techniques for acquiring and analyzing biophysical signals are described in particular for use in diagnosing the presence, non-presence, localization (where applicable), and/or severity of certain disease states or conditions in, associated with, or affecting, the cardiovascular (or cardiac) system, including for example pulmonary hypertension (PH), coronary artery disease (CAD), and heart failure (e.g., left-side or right-side heart failure).

Pulmonary hypertension, heart failure, and coronary artery disease are three diseases/conditions affiliated with the cardiovascular or cardiac system. Pulmonary hypertension (PH) generally refers to high blood pressure in the arteries of the lungs and can include a spectrum of conditions. PH typically has a complex and multifactorial etiology and an insidious clinical onset with varying severity. PH may progress to complications such as right heart failure and in many cases is fatal. The World Health Organization (WHO) has classified PH into five groups or types. The first PH group classified by the WHO is pulmonary arterial hypertension (PAH). PAH is a chronic and currently incurable disease that, among other things, causes the walls of the arteries of the lungs to tighten and stiffen. PAH requires at a minimum a heart catheterization for diagnosis. PAH is characterized by vasculopathy of the pulmonary arteries and defined, at cardiac catheterization, as a mean pulmonary artery pressure of 25 mm Hg or more. One form of pulmonary arterial hypertension is known as idiopathic pulmonary arterial hypertension—PAH that occurs without a clear cause. Among others, subcategories of PAH include heritable PAH, drug and toxin induced PAH, and PAH associated with other systemic diseases such as, e.g., connective tissue disease, HIV infection, portal hypertension, and congenital heart disease. PAH includes all causes that lead to the structural narrowing of the pulmonary vessels. With PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. The second PH group as classified by the WHO is pulmonary hypertension due to left heart disease. This group of disorders is generally characterized by problems with the left side of the heart. Such problems can, over time, lead to changes within the pulmonary arteries. Specific subgroups include left ventricular systolic dysfunction, left ventricular diastolic dysfunction, valvular disease and, finally, congenital cardiomyopathies and obstructions not due to valvular disease. Treatments of this second PH group tends to focus on the underlying problems (e.g., surgery to replace a heart valve, various medications, etc.). The third PH group as classified by the WHO is large and diverse, generally relating to lung disease or hypoxia. Subgroups include chronic obstructive pulmonary disease, interstitial lung disease, sleep breathing disorders, alveolar hypoventilation disorders, chronic high altitude exposure, and developmental lung disease. The fourth PH group is classified by the WHO as chronic thromboembolic pulmonary hypertension, caused when blood clots enter or form within the lungs, blocking the flow of blood through the pulmonary arteries. The fifth PH group is classified by the WHO as including rare disorders that lead to PH, such as hematologic disorders, systemic disorders such as sarcoidosis that have lung involvement, metabolic disorders, and a subgroup of other diseases. The mechanisms of PH in this fifth group are poorly understood.

PH in all of its forms can be difficult to diagnose in a routine medical examination because the most common symptoms of PH (shortness of breath, fatigue, chest pain, edema, heart palpitations, dizziness) are associated with so many other conditions. Blood tests, chest x-rays, electro- and echocardiograms, pulmonary function tests, exercise tolerance tests, and nuclear scans are all used variously to help a physician to diagnose PH in its specific form. As noted above, the "gold standard" for diagnosing PH, and for PAH in particular, is a cardiac catherization of the right side of the heart by directly measuring the pressure in the pulmonary arteries. If PAH is suspected in a subject, one of several investigations may be performed to confirm the condition, such as electrocardiography, chest radiography, and pulmonary function tests, among others. Evidence of right heart strain on electrocardiography and prominent pulmonary arteries or cardiomegaly on chest radiography is typically seen. However, a normal electrocardiograph and chest radiograph cannot necessarily exclude a diagnosis of PAH. Further tests may be needed to confirm the diagnosis and to establish cause and severity. For example, blood tests, exercise tests, and overnight oximetry tests may be performed. Yet further, imaging testing may also be performed. Imaging testing examples include isotope perfusion lung scanning, high resolution computed tomography, computed tomography pulmonary angiography, and magnetic resonance pulmonary angiography. If these (and possibly other) non-invasive investigations support a diagnosis of PAH, right heart catheterization typically is needed to confirm the diagnosis by directly measuring pulmonary pressure. It also allows measurement of cardiac output and estimation of left atrial pressure using pulmonary arterial wedge pressure. While non-invasive techniques exist to determine whether PAH may exist in a subject, these techniques cannot reliably confirm a diagnosis of PAH unless an invasive right heart catheterization is performed. Aspects and embodiments of methods and systems for assessing PH are disclosed in commonly-owned U.S. patent application Ser. No. 16/429, 593, the entirety of which is hereby incorporated by reference.

Heart failure affects almost 6 million people in the United States alone, and more than 870,000 people are diagnosed with heart failure each year. The term "heart failure" (sometimes referred to as congestive heart failure or CHF) generally refers to a chronic, progressive condition or process in which the heart muscle is unable to pump enough blood to meet the needs of the body, either because the heart muscle is weakened or stiff or because a defect is present that prevents proper circulation. This results in, e.g., blood and fluid backup into the lungs, edema, fatigue, dizziness, fainting, rapid and/or irregular heartbeat, dry cough, nausea and shortness of breath. Common causes of heart failure are coronary artery disease (CAD), high blood pressure, cardiomyopathy, arrhythmia, kidney disease, heart defects, obesity, tobacco use and diabetes. Diastolic heart failure (DHF), left- or left-sided heart failure/disease (also referred to as left ventricular heart failure), right- or right-sided heart failure/disease (also referred to as right ventricular heart failure) and systolic heart failure (SHF) are common types of heart failure.

Left-sided heart failure is further classified into two main types: systolic failure (or heart failure with reduced ejection fraction or reduced left ventricular function) and diastolic failure/dysfunction (or heart failure with preserved ejection fraction or preserved left ventricular function). Procedures and technologies commonly used to determine if a patient has left-sided heart failure include cardiac catheterization, x-ray, echocardiogram, electrocardiogram (EKG), electrophysiology study, radionucleotide imaging, and various treadmill tests, including a test that measures peak $VO_2$. Ejection fraction (EF), which is a measurement expressed as a percentage of how much blood a ventricle pumps out with each contraction (and in the case of left-sided heart failure the left ventricle), is most often obtained non-invasively via an echocardiogram. A normal left ventricular ejection fraction (LVEF) ranges from about 55% to about 70%.

When systolic failure occurs, the left ventricle cannot contract forcefully enough to keep blood circulating normally throughout the body, which deprives the body of a normal supply of blood. As the left ventricle pumps harder to compensate, it grows weaker and thinner. As a result, blood flows backwards into organs, causing fluid buildup in the lungs and/or swelling in other parts of the body. Echocardiograms, magnetic resonance imaging, and nuclear medicine scans (e.g., multiple gated acquisition) are techniques used to noninvasively measure ejection fraction (EF), expressed as a percentage of the volume of blood pumped by the left ventricle relative to its filling volume to aid in the diagnosis of systolic failure. In particular, left ventricular ejection fraction (LVEF) values below 55% indicate the pumping ability of the heart is below normal, and can in severe cases be measured at less than about 35%. In general, a diagnosis of systolic failure can be made or aided when these LVEF values are below normal.

When diastolic heart failure occurs, the left ventricle has grown stiff or thick, losing its ability to relax normally, which in turn means that the lower left chamber of the heart is unable to properly fill with blood. This reduces the amount of blood pumped out to the body. Over time, this causes blood to build up inside the left atrium, and then in the lungs, leading to fluid congestion and symptoms of heart failure. In this case, LVEF values tend to be preserved within the normal range. As such, other tests, such as an invasive catheterization may be used to measure the left ventricular end diastolic pressure (LVEDP) to aid in the diagnosis of diastolic heart failure as well as other forms of heart failure with preserved EF. Typically, LVEDP is measured either directly by the placement of a catheter in the left ventricle or indirectly by placing a catheter in the pulmonary artery to measure the pulmonary capillary wedge pressure. Such catheterization techniques, by their nature, increase the risk of infection and other complications to the patient and tend to be costly. As such, non-invasive methods and systems for determining or estimating LVEDP in diagnosing the presence or non-presence and/or severity of diastolic heart failure as well as myriad other forms of heart failure with preserved EF are desirable. In addition, non-invasive methods and systems for diagnosing the presence or non-presence and/or severity of diastolic heart failure as well as myriad other forms of heart failure with preserved EF, without necessarily including a determination or estimate of an abnormal LVEDP, are desirable. Embodiments of the present disclosure address all of these needs.

Right-sided heart failure often occurs due to left-sided heart failure, when the weakened and/or stiff left ventricle loses power to efficiently pump blood to the rest of the body. As a result, fluid is forced back through the lungs, weakening the heart's right side, causing right-sided heart failure. This backward flow backs up in the veins, causing fluid to swell in the legs, ankles, GI tract and liver. In other cases, certain lung diseases such as chronic obstructive pulmonary disease and pulmonary fibrosis can cause right-sided heart failure, despite the left side of the heart functioning normally. Procedures and technologies commonly used to determine if a patient has left-sided heart failure include a blood test, cardiac CT scan, cardiac catheterization, x-ray, coronary angiography, echocardiogram, electrocardiogram (EKG), myocardial biopsy, pulmonary function studies, and various forms of stress tests such as a treadmill test.

Pulmonary hypertension is closely associated with heart failure. As noted above, PAH (the first WHO PH group) can lead to an increased right ventricular afterload, right heart failure, and premature death. PH due to left heart failure (the second WHO PH group) is believed to be the most common cause of PH.

Ischemic heart disease, also known as cardiac ischemia or myocardial ischemia, and related condition or pathologies may also be estimated or diagnosed with the techniques disclosed herein. Ischemic heart disease is a disease or group of diseases characterized by a reduced blood supply to the heart muscle, usually due to coronary artery disease (CAD). CAD is closely related to heart failure and is its most common cause. CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmia. An arrhythmia is an abnormal heart rhythm and can include any change from the normal sequence of electrical conduction of the heart and in some cases can lead to cardiac arrest. The evaluation of PH, heart failure, CAD and other diseases and/or conditions can be complex, and many invasive techniques and tools are used to assess the presence and severity of the conditions as noted above. In addition, the commonalities among symptoms of these diseases and/or conditions as well as the fundamental connection between the respiratory and cardiovascular systems—due to the fact that they work together to oxygenate the cells and tissues of the body—point to a complex physiological interrelatedness that may be exploited to improve the detection and ultimate treatment of such diseases and/or conditions. Conventional methodologies to assess these biophysical signals in this context still pose significant challenges in giving healthcare providers tools for accurately detecting/diagnosing the presence or non-presence of such diseases and conditions.

For example, in electrocardiography—a field of cardiology in which the heart's electrical activity is analyzed to obtain information about its structure and function—it has been observed that significant ischemic heart disease can alter ventricular conduction properties of the myocardium in the perfusion bed downstream of a coronary artery narrowing or occlusion, the pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

In an aspect, a method is disclosed (e.g., to facilitates the configuration and training of a neural network (e.g., deep neural network, convolutional neural network (CNN), etc.), or ensemble(s) thereof, with a phase gradient biophysical signal data set (e.g., a wide-band phase gradient biophysical signal data set, a phase-gradient cardiac signal data set, a wide-band phase-gradient cardiac signal data set) to assess and/or classify coronary artery disease in a subject). The method includes receiving, by a processor, a biophysical signal data set of a subject acquired from one or more channels of one or more sensors; pre-processing the biophysical signal data set to generate one or more pre-processed data sets, wherein each pre-processed data set includes a single isolated complete cardiac cycle (e.g., wherein pre-processed data sets from each of the acquisition channels are phase synchronized/aligned); and determining, by the processor, a value (e.g., risk/likelihood, binary indication) indicative of presence or absence of cardiac disease or condition (e.g., coronary arterial disease, pulmonary hypertension, pulmonary arterial hypertension, left heart failure, right heart failure, and abnormal left-ventricular end diastolic pressure (LVEDP)) by directly inputting the pre-processed data set to one or more neural networks (e.g., one or more deep neural networks, one or more convolutional neural networks, etc.), or ensemble(s) thereof, trained with a set of training biophysical signal data set acquired from patients diagnosed with the cardiac disease or condition and labeled with the presence or non-presence of the cardiac disease or condition (e.g., wherein the label is based on a Gensini score or a binary values of location of disease in a coronary artery) (e.g., wherein the segmented data set are phase aligned among corresponding biophysical signal data set of other acquisition channels), wherein an output data set is outputted via a report and/or a display based on the determined value indicative of the presence of cardiac disease or condition (e.g., to assist or used in a diagnosis of presence or absence of cardiac disease or condition in the subject).

In some embodiments, the cardiac disease or condition is coronary artery disease, and wherein the step of determining the value indicative of the presence of cardiac disease or condition comprises inputting (e.g., directly inputting) the pre-processed data set to a set of one or more neural networks (e.g., a set of one or more deep neural networks, a set of one or more convolutional neural networks, etc.), or ensemble(s) thereof, trained with one or more biophysical signal data sets acquired from a plurality of subjects labeled with a diagnosis of presence or absence of coronary artery disease (e.g., significant coronary artery disease), (e.g., wherein the label for presence of coronary artery disease comprises a Gensini-based score determined as a combination of a severity weighted scoring and location weighted scoring for a coronary lesion diagnosed in the myocardium), wherein output of the one or more neural networks (e.g., output of the deep neural networks, output of the convolutional neural network, etc.), or ensemble(s) thereof, are outputted as the output data set via the report and/or the display.

In some embodiments, the biophysical signal data set is acquired from two or more acquisition channels and pre-processed data sets from each of the acquisition channels are phase synchronized.

In some embodiments, the step of pre-processing the biophysical signal data set comprises: segmenting, by the processor, a portion of the biophysical signal data set, or a normalized data set derived from the portion of the biophysical signal data set, associated with a first acquisition channel of the one or more acquisition channels, into one or more first segmented data sets, wherein each of the first segmented data sets includes the single isolated complete cardiac cycle (e.g., for a per-beat analysis) as a first single isolated completed cardiac cycle, wherein the first single isolated complete cardiac cycle has an associated time window; and segmenting, by the processor, another portion of the biophysical signal data set, or a normalized data set derived from the another portion of the biophysical signal data set, associated with a second acquisition channel of the one or more acquisition channels, into one or more second segmented data sets, wherein each of the one or more second segmented data sets include a second single isolated complete cardiac cycle, wherein the second single isolated complete cardiac cycle has an associated time window corresponding to that of the first single isolated complete cardiac cycle to provide phase synchronized data sets.

In some embodiments, the label for presence of coronary artery disease comprises a Gensini-based score determined as a combination of a severity weighted scoring and location weighted scoring for a coronary lesion diagnosed in the myocardium.

In some embodiments, the Gensini-based score is linearized (e.g., via a logarithmic operator).

In some embodiments, the method includes determining, by the processor, one or more location values indicative of presence or absence of cardiac disease or condition at a given coronary artery by inputting (e.g., directly inputting) the pre-processed data set, or a modified version of the pre-processed data set, to one or more second neural networks (e.g., one or more second deep neural networks, one or more second convolutional neural networks, etc.), or ensemble(s) thereof, trained with one or more biophysical signal data sets (e.g., a coronary-artery-disease localization array) acquired from a plurality of subjects labeled (e.g., binary labels) with a diagnosis of presence or absence of coronary artery disease located at a coronary artery selected from the group consisting of a left main artery (LMA), a proximal left circumflex artery (Prox LCX), a mid-left circumflex artery (mid LCX), a distal left circumflex artery (Dist LCX), a LPAV, a first obtuse marginal (OM1), a second obtuse marginal (OM2), a third obtuse marginal (OM3), a proximal left anterior descending artery (Prox LAD), a mid left anterior descending artery (Mid LAD), a distal left anterior descending artery (Dist LAD), LAD D1, LAD D2, a proximal right coronary artery (Prox RCA), a mid-right coronary artery (Mid RCA), a distal right coronary artery (Dist RCA), and an acute marginal branch right of the posterior descending artery (AcM R PDA), wherein the determined one or more location values are outputted as the output data set via the report and/or the display.

In some embodiments, the method further includes comparing, by the processor, the value (e.g., risk/likelihood, binary indication) indicative of the presence of cardiac disease or condition to a threshold value, wherein the step of determining the one or more location values indicative of the presence of cardiac disease or condition at the given coronary artery is performed based on the comparison (e.g., wherein the value indicative of the presence of cardiac disease or condition indicates a positive state for the presence of the cardiac disease or condition).

In some embodiments, the method further includes performing, by the processor, a phase space operation of the received biophysical signal data set or the pre-processed data set to generate one or more phase space data sets/images; and outputting, by the processor, the one or more generated phase space data sets/images, wherein the one or more generated phase space data sets/images are concurrently and/or simultaneously presented in the report and/or display with the output data set.

In some embodiments, the step of pre-processing the biophysical signal data set to generate one or more pre-processed data sets further comprises a second pre-processing operation selected from the group consisting of: performing a down-sampling operation; and performing a baseline wander removal operation; and performing a normalization operation (e.g., to normalize data set between 0 and 1).

In some embodiments, at least one of the one or more neural networks (e.g., one or more deep neural networks, one or more convolutional neural networks, etc.), or ensemble(s) thereof, is configured based on a hyperparameter search loop, wherein implementation of the hyperparameter search loop comprises: generating, by the processor, a plurality of hyperparameter sets for a template neural network (e.g., a template deep neural network, a template convolutional neural network, a template for an ensemble thereof, etc.), wherein each of the plurality of hyperparameter sets is generated by a random, or pseudo-random selection, from a set of candidate hyperparameters, wherein at least one hyperparameter of the set of candidate hyperparameters is selected from the group consisting of: batch size, learning rate, convolutional layer, filter size, a number of filter in a first convolutional layer, an increase in filter in subsequent layer(s), number of additional dense layers, size of additional dense layers, activation function type, target, dilation rate, and dropout; training, by the processor, for each of plurality of hyperparameter sets, the template neural network, wherein in each instance of the evaluation, the template neural network is configured with a hyperparameter set of the plurality of hyperparameter sets; and evaluating, by the processor, for each of plurality of hyperparameter sets, the trained neural network (e.g., trained deep neural network, trained convolutional neural network, etc.), or ensemble(s) thereof, with a first validation data set, wherein each evaluation generates a score (e.g., an "area under the curve" or AUC score or a true-AUC score).

In some embodiments, the at least one of the one or more neural networks (e.g., one or more deep neural networks, one or more convolutional neural networks, etc.), or ensemble(s) thereof, is configured based on a Bayesian hyperparameter optimization.

In some embodiments, the evaluation of the trained neural network (e.g., the trained deep neural network, convolutional neural network, etc.), or ensemble(s) thereof, include generating an accuracy score, a weighted accuracy score, a positive predictive score, a negative predictive score, a F-score, a sensitivity score, a specificity score, and/or a diagnostic odds ratio score.

In some embodiments, at least one of the one or more second neural networks (e.g., one or more second deep neural networks, one or more second convolutional neural network, etc.), or ensemble(s) thereof, is configured based on a hyperparameter search loop (e.g., wherein at least one hyperparameter of a set of hyperparameters used in the configuration is selected from the group consisting of: batch size, learning rate, convolutional layer, filter size, a number of filter in a first convolutional layer, an increase in filter in subsequent layer, stride, number of additional dense layers, size of additional dense layers, activation function type, size of max pooling, dropout, and loss function).

In some embodiments, the one or more biophysical signal data sets acquired from the plurality of patients labeled with the diagnosis of presence or absence of coronary artery disease located at a coronary artery is configures as a coronary-artery-disease localization array, and wherein the localization array comprise a plurality of elements each corresponding to a label indicative of presence or non-presence of the cardiac disease or condition at a given location in the coronary artery.

In some embodiments, the method further includes modifying the value indicative of presence of cardiac disease or condition based one or more additional predictive models, wherein the one or more additional predictive models involve analysis based on geometric features associated with geometric shape or topology of the biophysical signal data set in phase space.

In some embodiments, the method further includes merging the value indicative of presence of cardiac disease or condition with a second predictive value indicative of presence of cardiac disease or condition, wherein the second predictive value indicative of presence of cardiac disease or condition is based one or more additional predictive models, wherein the one or more additional predictive models involve analysis based on geometric features associated with geometric shape or topology of the biophysical signal data set in phase space.

In some embodiments, the geometric features associated with geometric shape or topology of the biophysical signal data set in phase space comprise at least one of: VDfA-B feature, VDp feature, VR_VDO_A-B feature, VDT_A-B feature, mADa feature, VRcVDcPA-C feature, AD_VR_A feature, tnVDp feature, VDTA-A feature, tnVRp feature, VR_VDO_A-A feature, LCXp feature, VDfA-A feature, rA-D feature, rA-C feature, rA-B feature, rA-A feature, and VRc_VDcPA-A feature.

In some embodiments, the VDp feature is a quantification of the biophysical signal data set in a region in phase space occupied by identified ventricular depolarization trajectories.

In some embodiments, the VDFA feature is a quantification of fiducial points of the biophysical signal data set in the phase space, wherein the fiducial points comprise at least one of a machine-identified maximal ventricular depolarization, a machine-identified point prior to the maximal ventricular depolarization, and a machine-identified conclusion of ventricular depolarization.

In another aspect, a method is disclosed comprising the steps of receiving, by a processor, a biophysical signal data set of a subject, wherein the biophysical signal data set is associated with a plurality of phase-gradient cardiac signals simultaneously acquired via a corresponding number of acquisition channels from the subject via at least one electrode; pre-processing the biophysical signal data set from at least one of the acquisition channels to generate one or more pre-processed data sets, wherein each pre-processed data set includes a single isolated complete cardiac cycle; and determining, by the processor, a value (e.g., risk/likelihood, binary indication) indicative of the presence or absence of cardiac disease or other condition (e.g., coronary arterial disease, pulmonary hypertension, pulmonary arterial hypertension, left heart failure, right heart failure, and abnormal left-ventricular end diastolic pressure (LVEDP)) by directly inputting the pre-processed data set to a set of one or more neural networks (e.g., a set of one or more deep neural networks, a set of one or more convolutional neural networks, etc.), or ensemble(s) thereof, trained with one or more biophysical signal data sets (e.g., one or more phase gradient biophysical-signal data et, one or more phase gradient cardiac signal data set, etc.) acquired from a plurality of patients or subjects each labeled with a diagnosis of presence of coronary artery disease in the patient or subject (e.g., significant coronary artery disease), (e.g., wherein the label for presence of coronary artery disease comprises a Gensini-based score determined as a combination of a severity weighted scoring and location weighted scoring for a coronary lesion diagnosed in the myocardium, and wherein the pre-processed data sets of a given acquisition channel are segmented in a phase-aligned manner to corresponding biophysical signal data set of other acquisition channels); wherein an output data set is outputted via a report and/or a display based on the determined value indicative of a binary presence of cardiac disease or condition.

In another aspect, a method is disclosed comprising the steps of receiving, by a processor, a biophysical signal data set of a subject, wherein the biophysical signal data set is associated with a plurality of phase-gradient cardiac signals simultaneously acquired via a corresponding number of acquisition channels from the subject via at least one electrode; and determining, by the processor, one or more location values indicative of presence of cardiac disease or condition at one or more coronary arteries by inputting (e.g., directly inputting) the pre-processed data set, or a modified version of the pre-processed data set, to one or more second neural networks (e.g., one or more second deep neural network, one or more second convolutional neural networks, etc.), or ensemble(s) thereof, trained with one or more biophysical signal data sets (a coronary-artery-disease localization array) acquired from a plurality of patients or subjects each labeled with a diagnosis of presence and/or absence of coronary artery disease located at a coronary artery, or associated myocardium region(s), selected from the group consisting of a left main artery (LMA), a proximal left circumflex artery (Prox LCX), a mid-left circumflex artery (mid LCX), a distal left circumflex artery (Dist LCX), a LPAV, a first obtuse marginal (OM1), a second obtuse marginal (OM2), a third obtuse marginal (OM3), a proximal left anterior descending artery (Prox LAD), a mid-left anterior descending artery (Mid LAD), a distal left anterior descending artery (Dist LAD), LAD D1, LAD D2, a proximal right coronary artery (Prox RCA), a mid-right coronary artery (Mid RCA), a distal right coronary artery (Dist RCA), and an acute marginal branch right of the posterior descending artery (AcM R PDA), wherein an output data set is outputted via a report and/or a display based on the determined value indicative of the presence of cardiac disease or condition at the one or more coronary arteries.

In another aspect, a method is disclosed of configuring a neural network (e.g., deep neural network, convolutional neural network, etc.), or ensemble(s) thereof, to detect presence of coronary arterial disease or a condition or to estimate the localization of coronary arterial disease or condition in a subject. The method includes generating, by the processor, a plurality of hyperparameter sets for a template neural network (e.g. a template deep neural network, a template convolutional neural network, etc.), wherein each of the plurality of hyperparameter sets is generated by a random, or pseudo-random selection, from a set of hyperparameters, wherein at least one hyperparameter of the set of hyperparameters is selected from the group consisting of: batch size, learning rate, convolutional layer, filter size, a number of filter in a first convolutional layer, an increase in filter in subsequent layer, number of additional dense layers, size of additional dense layers, activation function type, target, dilation rate, and dropout; training, by the processor, for each of plurality of hyperparameter sets, the template neural network, wherein in each instance of the evaluation, the template neural network (e.g., template deep neural network, template convolutional neural network, etc.) is configured with a hyperparameter set of the plurality of hyperparameter sets; and evaluating, by the processor, for each of plurality of hyperparameter sets, the trained neural network (e.g., trained deep neural network, trained convolutional neural network, etc.) with a first validation data set, wherein each evaluation generates a score (e.g., an AUC score or a true-AUC score), wherein the trained neural network (e.g., trained deep neural network, trained convolutional neural network, etc.) is subsequently used to diagnose the presence and/or the localization of coronary arterial disease in the subject.

In some embodiments, the evaluation of the trained neural network (e.g., trained deep neural network, trained convolutional neural network, etc.) include generating an accuracy score, a weighted accuracy score, a positive predictive score, a negative predictive score, a F-score, a sensitivity score, a specificity score, and/or a diagnostic odds ratio score.

In another aspect, a system is disclosed comprising one or more processors; and a memory having instructions stored thereon, wherein execution of the instruction by the one or more processors cause the one or more processors to perform any one of the above-recited method.

In another aspect, a system is disclosed comprising: a device configured to acquire phase-gradient biophysical signals (e.g., a wide-band phase gradient biophysical signal data set, a phase-gradient cardiac signal data set, a wide-band phase-gradient cardiac signal data set, etc.); and an assessment system coupled, directly or indirectly, to said device. The assessment system includes one or more processors; and a memory having instructions stored thereon, wherein execution of the instruction by the one or more processors cause the one or more processors to perform any one of the method of the above-recited method.

In another aspect, a system is disclosed comprising: a storage area network configured to receive and store acquire phase-gradient biophysical signal data set (e.g., a wide-band phase gradient biophysical signal data set, a phase-gradient cardiac signal data set, a wide-band phase-gradient cardiac signal data set, etc.) generated from a device configured to acquire wide-band phase-gradient signals; and an assessment system coupled, directly or indirectly, to said storage area network, the assessment system comprising: one or more processors; and a memory having instructions stored thereon, wherein execution of the instruction by the one or more processors cause the one or more processors to perform any one of the method of the above-recited method.

In another aspect, a non-transitory computer readable medium is disclosed, the computer readable medium having instructions stored thereon, wherein execution of the instruction by one or more processors, cause the one or more processors to perform any one of the method of the above-recited method.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 6 shows executable code to construct a neural network model (e.g., a deep neural network model, a convolutional neural network model, etc.) from a set of randomly selected hyperparameters, in accordance with an illustrative embodiment.

DETAILED SPECIFICATION

Each and every feature described herein, and each and every combination of two or more of such features, is included within the scope of the present invention provided that the features included in such a combination are not mutually inconsistent.

While the present disclosure is directed to the beneficial assessment of biophysical signals in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), left heart failure, right-sided heart failure, and abnormal left-ventricular end diastolic pressure (LVEDP), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

Example System

Figure 1:
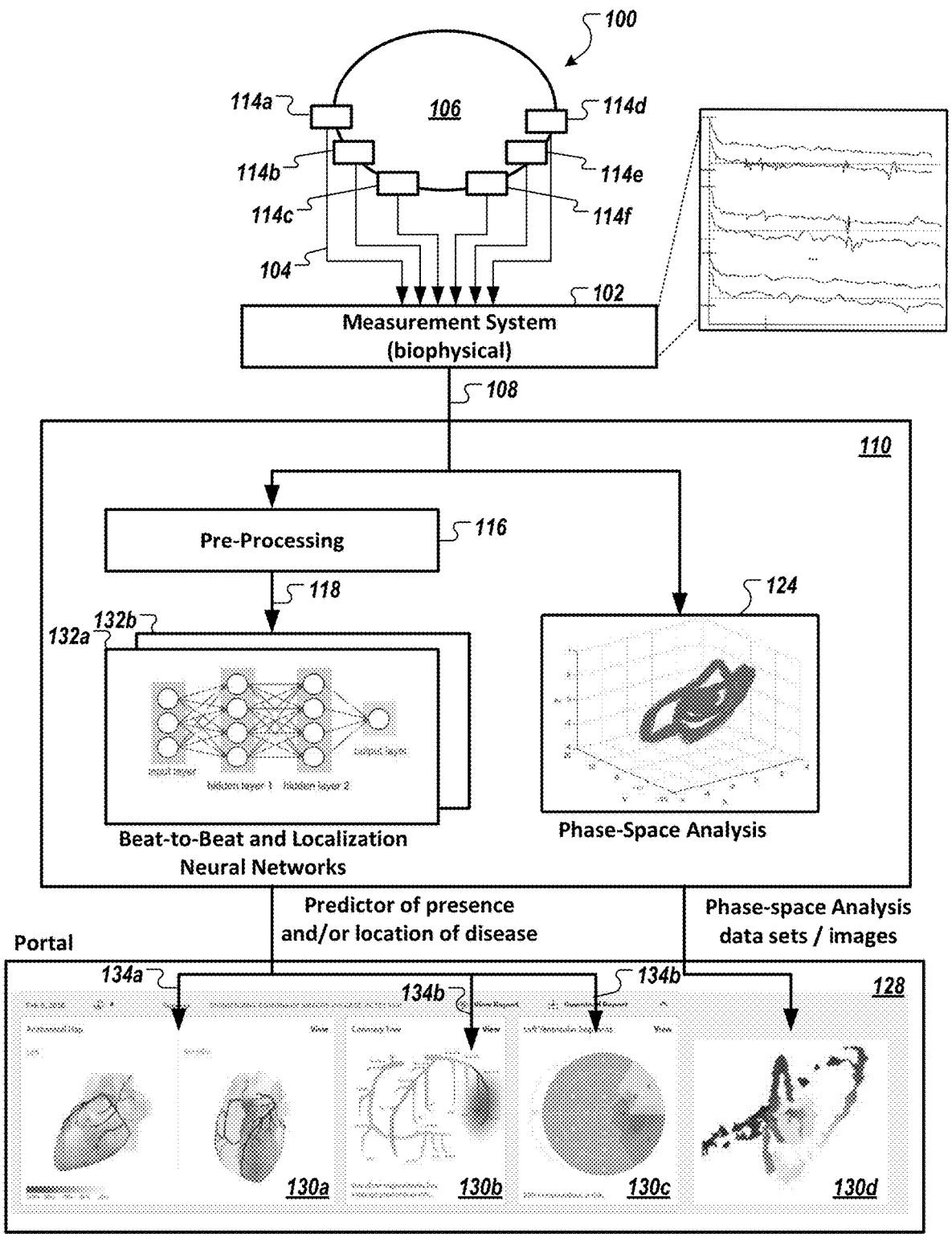
FIG. 1 is a diagram of an exemplary system configured to non-invasively assess presence or non-presence of coronary artery disease in a person using a neural network (e.g., a deep neural network, a convolutional neural network, etc.), or ensemble(s) thereof, in accordance with an illustrative embodiment.

FIG. 1 is a diagram of an exemplary system 100 configured to assess (e.g., non-invasively assess) presence or non-presence of coronary artery disease in a person using a neural network (e.g., a deep neural network, a convolutional neural network, etc.), in accordance with an illustrative embodiment. As noted herein, physiological systems can refer to the cardiovascular system, the pulmonary system, the renal system, the nervous system, and other functional systems and sub-systems of the body. In the context of the cardiovascular system, the particular embodiment of system 100 shown in FIG. 1 facilitates the investigation of complex, nonlinear systems of the heart by examining in phase space the states, or phases, that such a system may exhibit over many cycles.

In FIG. 1, measurement system 102 is a non-invasive embodiment (shown as "Measurement System (biophysical)" 102) that acquires a plurality of biophysical signals 104 (e.g., phase-gradient biophysical signals) via any number of measurement probes 114 (shown as probes 114a, 114b, 114c, 114d, 114e, and 114f) from a subject 106 to produce a biophysical data set 108. The biophysical signal data set 108 includes a plurality of acquired signals (e.g., acquired from three distinct channels), which can be combined together to generate a multi-dimensional data set, e.g., a three-dimensional phase space representation, of the biophysical-signal data set 108. Measurement system 102 is configured to transmit, e.g., over a communication system and/or network, or via a direct connection, the acquired biophysical-signal data set 108, or a data set derived or processed therefrom, to a repository (e.g., a storage area network) (not shown) that is accessible to a non-invasive biophysical-signal assessment system 110) to be evaluated by an analytic engine executing a phase space analysis of the deterministic chaos or quasi-periodic characteristics of the acquired biophysical-signal data set 108 to determine a clinical output 112 (includes an assessment of the presence or non-presence of a disease and/or an estimated physiological characteristic of the physiological system under study). In some embodiments, the clinical output includes an assessment of the presence or non-presence of a disease, condition and/or an estimated physiological characteristic of the physiological system under study. In other embodiments, there is no clinical output but rather output of information that may be used by a clinician to provide their own clinical assessment of the information relative to the patient whose signals are being assessed.

Measurement system 102, in some embodiments, is configured to acquire biophysical signals that may be based on the body's biopotential via biopotential sensing circuitries as biopotential biophysical signals. In the cardiac and/or electrocardiography contexts, measurement system 102 is configured to capture cardiac-related biopotential or electrophysiological signals of a living subject (such as a human) as a biopotential cardiac signal data set. In some embodiments, measurement system 102 is configured to acquire a wide-band cardiac phase gradient signals as a biopotential signal or other signal types (e.g., a current signal, an impedance signal, a magnetic signal, an optical signal, an ultrasound or acoustic signal, etc.). The term "wide-band" in reference to an acquired signal, and its corresponding data set, refers to the signal having a frequency range that is substantially greater than the Nyquist sampling rate of the highest dominant frequency of a physiological system of interest. For cardiac signals, which typically has a dominant frequency components between about 0.5 Hz and about 80 Hz, the wide-band cardiac phase gradient signals or wide-band cardiac biophysical signals comprise cardiac frequency information at a frequency selected from the group consisting between about 0.1 Hz and about 1 KHz, between about 0.1 Hz and about 2 KHz, between about 0.1 Hz and about 3 KHz, between about 0.1 Hz and about 4 KHz, between about 0.1 Hz and about 5 KHz, between about 0.1 Hz and about 6 KHz, between about 0.1 Hz and about 7 KHz, between about 0.1 Hz and about 8 KHz, between about 0.1 Hz and about 9 KHz, between about 0.1 Hz and about 10 KHz, and between about 0.1 Hz and greater than 10 KHz (e.g., 0.1 Hz to 50 KHz or 0.1 Hz to 500 KHz). In addition to capturing the dominant frequency components, the wide-band acquisition also facilitate capture of other frequencies of interest. Examples of such frequencies of interest can include QRS frequency profiles (which can have frequency ranges up to 250 Hz), among others. The term "phase gradient" in reference to an acquired signal, and corresponding data set, refers to the signal being acquired at different vantage points of the body to observe phase information for a set of distinct events/functions of the physiological system of interest. Following the signal acquisition, the term "phase gradient" refers to the preservation of phase information via use of non-distorting signal processing and pre-processing hardware, software, and techniques (e.g., phase-linear filters and signal-processing operators and/or algorithms).

In the neurological context, measurement system 102 is configured to capture neurological-related biopotential or electrophysiological signals of a living subject (such as a human) as a neurological biophysical signal data set. In some embodiments, measurement system 102 is configured to acquire wide-band neurological phase gradient signals as a biopotential signal or other signal types (e.g., a current signal, an impedance signal, a magnetic signal, an ultrasound, an optical signal, an ultrasound or acoustic signal, etc.). Examples of measurement system 102 are described in U.S. Publication No. 2017/0119272 and in U.S. Publication No. 2018/0249960, each of which is incorporated by reference herein in its entirety.

In some embodiments, measurement system 102 is configured to capture wide-band biopotential biophysical phase gradient signals as unfiltered electrophysiological signals such that the spectral component(s) of the signals are not altered. Indeed, in such embodiments, the wide-band biopotential biophysical phase gradient signals are captured, converted, and even analyzed without having been filtered (via, e.g., hardware circuitry and/or digital signal processing techniques, etc.) (e.g., prior to digitization) that otherwise can affect the phase linearity of the biophysical signal of interest. In some embodiments, the wide-band biopotential biophysical phase gradient signals are captured in microvolt or sub-microvolt resolutions that are at, or significantly below, the noise floor of conventional electrocardiographic, electroencephalographic, and other biophysical-signal acquisition instruments. In some embodiments, the wide-band biopotential biophysical signals are simultaneously sampled having a temporal skew or "lag" of less than about 1 microseconds, and in other embodiments, having a temporal skew or lag of not more than about 10 femtoseconds. Notably, the exemplified system minimizes non-linear distortions (e.g., those that can be introduced via certain filters) in the acquired wide-band phase gradient signal to not affect the information therein.

Referring still to FIG. 1, an assessment system 110 includes a Pre-Processing module 116 configured, in the context of cardiac signals, to receive and pre-process the acquired biophysical-signal data set 108 to generate one or more pre-processed data sets 118 each having a set of single isolated complete cardiac cycles as beat-to-beat cardiac data sets.

Assessment system 110 includes a first set of one or more neural networks 132a (e.g., one or more deep neural network(s), one or more convolutional neural network(s), etc.), or ensemble(s) thereof, each trained in this embodiment with a set of training cardiac signal data sets acquired from patients or subjects diagnosed with a cardiac disease or condition. Assessment system 110, in some embodiments, and as shown in FIG. 1, includes a second set of one or more neural networks 132b (e.g., a second set of one or more deep neural networks, a second set of one or more convolutional neural networks, etc.), or ensemble(s) thereof, each trained in this embodiment with a set of training cardiac signal data set acquired from patients diagnosed with the cardiac disease or condition and labeled with a presence/location and/or non-presence/non-location of the cardiac disease or condition in a region of the myocardium or a particular coronary artery (e.g., from a set of coronary arteries). The one or more neural networks 132a, in some embodiments, receive(s) the pre-processed data sets 118 to train a classifier and/or to perform a classification on the received input. When used for classification, the output of the first set of one or more neural networks 132a (e.g., one or more deep neural network(s), one or more convolutional neural network(s), etc.), or ensemble(s) thereof, in some embodiments, is a value (134a), e.g., a binary value or a risk/likelihood score, that indicates presence of cardiac disease or condition. The output of the second set of one or more neural networks 132b (e.g., one or more deep neural network(s), one or more convolutional neural network(s), etc.), or ensemble(s) thereof, in some embodiments, is a value (134b), e.g., a binary value or a risk/likelihood score, that indicates presence/location of cardiac disease or condition at a region of the myocardium and/or a location in the coronary artery. In some embodiments, the outputs 134a and 134b are generated from the same one or more neural networks (e.g., 132a or 132b) (e.g., one or more deep neural network(s), one or more convolutional neural network(s), etc.), or ensemble(s) thereof.

As used herein, the term "neural network" (and artificial neural networks (ANN)) refers to a family or framework of machine learning algorithms inspired by biological neural networks that can be instantiated in computing hardware and trained to perform tasks, including to learn on a set of features generated from a training set of data, e.g., to optimize one or more predictive models, which can be applied to data sources with unknown outcomes. Neural networks with fully-connected layers can define a family of functions that are parameterized by the weights of the network elements. Deep neural networks are examples of such multi-layer interconnected neural networks configured to recognize patterns directly from data sets with minimal preprocessing. Examples of classes of deep neural networks includes, for example, but not limited to, feed-forward neural networks, recurrent neural network, multi-layer perceptrons (MLP), convolutional neural networks, recursive neural networks, deep belief networks, convolutional deep belief networks, self-organizing maps, deep Boltzmann machines, stacked de-noising auto-encoders, etc. Convolutional neural networks ("CNNs"), and the likes, are particularly optimized to recognize patterns directly from a multi-dimensional data set (e.g., images). Examples of popular convolutional neural networks include GoogLeNets, ResNets, ResNeXts, DenseNets, DualPathNets, etc., each of which can be applied to the prediction or estimation of presence or absence of a disease state. The neural network, in some embodiments, uses deep learning methods such as CNNs to classify multi-dimensional data sets into one or more positive classes and/or one more negative classes based on machine-extractable features. As used herein, reference(s) to one or more neural network(s) can include one or more instance(s) of neural network architecture of the same type as well as instances of one or more instance(s) or combination(s) of neural network architectures of different types.

Description of neural networks are published at http://cs231n.github.io/neural-networks-1/ and training of convolutional neural networks is published at http://cs231n.github.io/convolutional-networks/, which are incorporated by reference herein in their entirety.

In FIG. 1, system 100, in some embodiments, includes a healthcare provider portal (shown as "Portal" 128) configured to display the output of the neural network(s) (e.g., 134a, 134b) (among other data sets) in, or along with, a phase space analysis report and/or angiographic-equivalent report. Portal 128, which in some embodiments may be termed a physician or clinician portal 128, is configured to access, retrieve, and/or display or present reports and/or the output of the neural network(s) (e.g., 134a, 134b) (and other data) for the report) from a repository (e.g., a storage area network).

In some embodiments, and as shown in FIG. 1, the healthcare provider portal 128 is configured to display the output of the neural network(s) (e.g., 134a, 134b) (e.g., deep neural network(s), convolutional neural network(s), etc.), or ensemble(s) thereof, in, or along with, an anatomical mapping report 130a, a coronary tree report 130b, and/or a 17-segment report 130c. Portal 128 may present the data, e.g., in real-time (e.g., as a web object), as an electronic document, and/or in other standardized or non-standardized image visualization/medical data visualization/scientific data visualization formats. The healthcare provider portal 128 and/or repository can be compliant with patient information and other personal data privacy laws and regulations (such as, e.g., the U.S. Health Insurance Portability and Accountability Act of 1996 and the EU General Data Protection Regulation) and laws relating to the marketing of medical devices (such as, e.g., the US Federal Food and Drug Act and the EU Medical Device Regulation). Further description of an example healthcare provider portal 128 is provided in U.S. Publication No. 2018/0078146, title "Method and System for Visualization of Heart Tissue at Risk", which is incorporated by reference herein in its entirety. Although in certain embodiments, the healthcare provider portal 128 is configured for presentation of patient medical information to healthcare professionals, in other embodiments, Portal 128 can be made accessible to and useful for patients, researchers, academics, and/or other portal users.

The anatomical mapping report 130a, in some embodiments, includes one or more depictions of a rotatable and optionally scalable three-dimensional anatomical map of cardiac regions of affected myocardium. The anatomical mapping report 130a, in some embodiments, is configured to display and switch between a set of one or more three-dimensional views and/or a set of two-dimensional views of a model having identified regions of myocardium. The coronary tree report 130b, in some embodiments, includes one or more two-dimensional view of the major coronary artery. The 17-segment report 130c, in some embodiments, includes one or more two-dimensional 17-segment views of corresponding regions of myocardium. In each of the report, the value (134b) that indicates presence of cardiac disease or condition at a location in the myocardium, as well as a label indicating presence of cardiac disease (134a), may be rendered as both static and dynamic visualization elements that indicates area of predicted blockage, for example, with color highlights of a region of affected myocardium and with an animation sequence that highlight region of affected coronary arter(ies). In some embodiments, each of the report includes textual label to indicate presence or non-presence of cardiac disease (e.g., presence of significant coronary artery disease) as well as a textual label to indicate presence (i.e., location) of the cardiac disease in a given coronary artery disease.

In the context of cardiovascular systems, in some embodiments, the healthcare provider portal (and corresponding graphic user interface) is configured to present summary information visualizations of myocardial tissue that identifies myocardium at risk and/or coronary arteries that are blocked. The user interface can be a graphical user interface ("GUI") with a touch- or pre-touch sensitive screen with input capability. The user interface can be used, for example, to direct diagnostics and treatment of a patient and/or to assess patients in a study. The visualizations, for a given report of a study, may include multiple depictions of a rotatable three-dimensional anatomical map of cardiac regions of affected myocardium, a corresponding two-dimensional view of the major coronary arteries, and a corresponding two-dimensional 17-segment view of the major coronary arteries to facilitate interpretation and assessment of architectural features of the myocardium for characterizing abnormalities in the heart and in cardiovascular functions. The visualizations, for a given report of a study, may include multiple depictions of the output of the neural network(s) (e.g., 134a, 134b) (e.g., one or more deep neural network(s), one or more convolutional neural network(s), etc.), or ensemble(s) thereof, e.g., as a textual label to indicate presence or non-presence of cardiac disease (e.g., presence of significant coronary artery disease) as well as a textual label to indicate presence (i.e., location) of the cardiac disease in a given coronary artery disease and/or associated myocardium region(s).

To generate the phase space volumetric data sets/images, the system as shown in FIG. 1 includes a phase space analysis module 124. The phase space analysis module 124, in some embodiments, facilitates the isolation of the deterministic chaos of the physiological system from other types of physiological behavior to be displayed as a functional quantification (e.g., as a phase space analysis data set/image), versus an anatomical one, of the physiological system. The phase space analysis module 124, in some embodiments, is configured to use a model (e.g., generated from a sparse approximation algorithm, such as matching pursuit) to estimate and/or predict the deterministic chaos within the pre-processed biophysical signal data set 118 (or the acquired biophysical signal data set 108) as a residue of the pre-processed biophysical signal data set, e.g., subtracted by the model. To model the deterministic chaotic behavior and/or characteristics of the physiological system, the analytical engine of the assessment system 110 is configured to accurately model acquired biophysical-signal data set (e.g., greater than 95% accuracy). In some embodiments, the model was generated from a modeling algorithm (e.g., sparse approximation algorithm) has a modeling accuracy greater than 99%. In some embodiments, the modeling algorithm has an accuracy greater than 99.9%. In some embodiments, the modeling algorithm has an accuracy greater than 99.99%. In some embodiments, the modeling algorithm has an accuracy greater than 99.999%. In some embodiments, the modeling algorithm has an accuracy greater than 99.9999%. In some embodiments, the modeling algorithm is configured to iteratively and recursively select candidate basis functions to add to the model until a stopping condition is reached (e.g., an assessed accuracy value reaches a pre-defined accuracy value (e.g., X %), the model reaches a maximum allowable number of candidates, and/or the model has included all available candidates).

Examples of useful phase space concepts and analysis are described in U.S. Publication No. 2018/0000371, entitled "Non-invasive Method and System for Measuring Myocardial Ischemia, Stenosis Identification, Localization and Fractional Flow Reserve Estimation"; U.S. Publication No. 2019/0214137, entitled "Method and System to Assess Disease Using Phase Space Volumetric Objects," filed Dec. 26, 2018; U.S. Publication No. 2019/0200893, entitled "Method and System to Assess Disease Using Phase Space Tomography and Machine Learning," each of which is incorporated by reference.

Predictor of Coronary Artery Disease Using Neural Networks

Figure 2A:
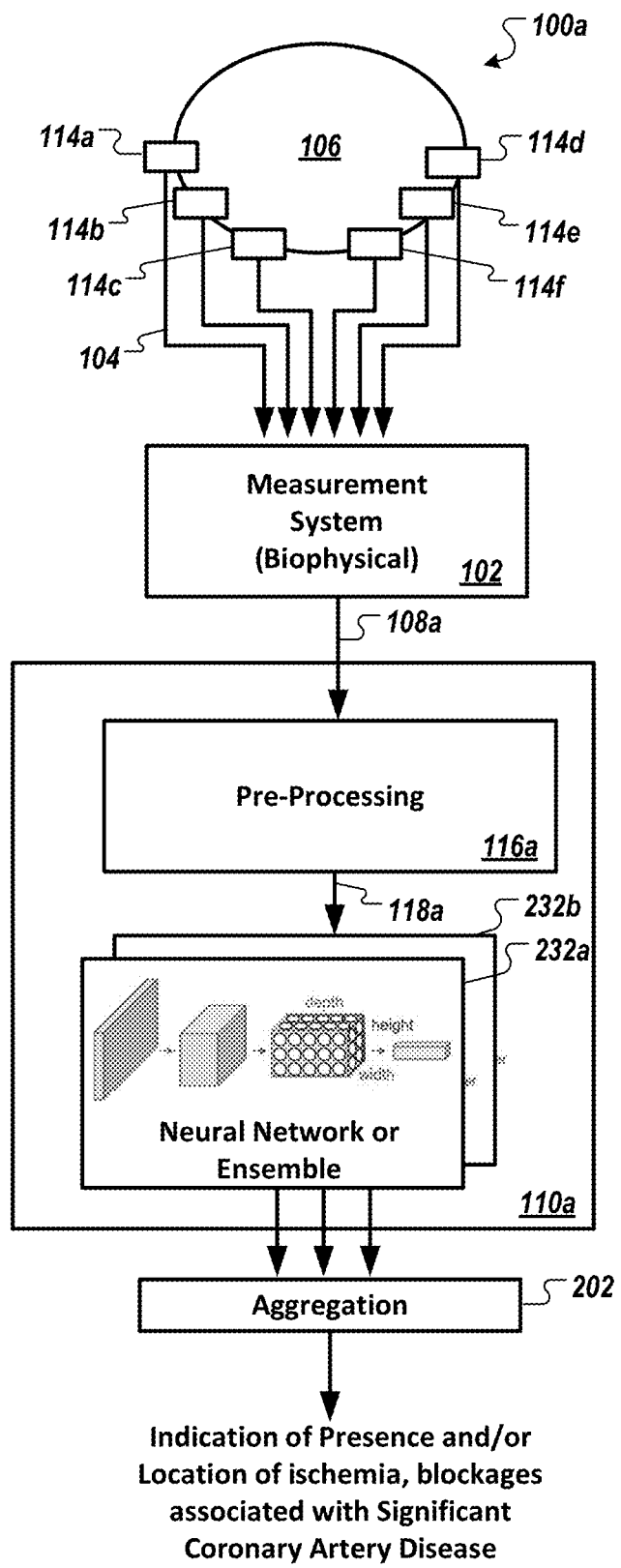
FIG. 2A is a diagram of a system comprising one or more neural network(s) (e.g., one or more deep neural network(s), one or more convolutional neural network(s), etc.), or ensemble(s) thereof, configured to predict presence of coronary artery disease or a condition, in accordance with an illustrative embodiment in the cardiovascular context.

FIG. 2A is a diagram of a system 100a comprising one or more neural network(s) 232a, 232b (e.g., one or more deep neural networks, one or more convolutional neural networks, etc.), or ensemble(s) thereof, configured to predict presence of coronary artery disease (e.g., in a patient and/or in a location of the coronary artery, in accordance with an illustrative embodiment in the cardiovascular context. Other neural networks 132, 132b (e.g., deep neural networks, convolutional neural networks, etc.), or ensemble(s) thereof, as described in relation to FIG. 1 can be used as a substitute for 232a, 232b.

Convolutional neural networks, such as GoogLeNets, ResNets, ResNeXts, DenseNets, DualPathNets, comprise an architecture that may include one or more input layers, one or more CONV layers (e.g., configure to compute a dot product between weights of individual neurons and a small region of connection), one or more RELU/ELU layers (e.g., includes elementwise activation function), one or more POOL layers (e.g., includes a down-sampling operator), and one or more FC (fully-connected) layers (e.g., includes a class scoring computation), etc.

As shown in FIG. 2A, the non-invasive measurement system 102 acquires a plurality of biophysical signals 104 via measurement probes or electrodes 114 (shown as probes 114a, 114b, 114c, 114d, 114e, and 114f) across a plurality of channels from a subject 106 to produce a biophysical data set 108a.

Following acquisition, assessment system 110a receives the biophysical data set 108a directly, or indirectly over a network (i.e., communication network) or a data repository comprising a storage area network, from the measurement system 102. Assessment system 110a includes a Pre-Processing module 116a and a set of one or more neural networks 232a, 232b (e.g., one or more deep neural networks, one or more convolutional neural networks, etc.) or ensemble(s) thereof, each trained with a set of training biophysical-signal data (e.g., phase gradient biophysical data set, wide-band phase gradient biophysical signal data set) acquired from patients diagnosed with the cardiac disease or condition and labeled with the presence in a patient and/or presence/non-presence of the cardiac disease or condition in a particular coronary artery (e.g., from a set of coronary arteries).

The Pre-Processing module 116a is configured, in the cardiovascular context, to pre-process (via, e.g., a phase-linear pre-processing technique) the biophysical data set 108a from at least one of the acquisition channels to generate one or more pre-processed data sets 118a from each acquired channel in which each pre-processed data set 118a includes a single isolated complete cardiac cycle and is phase-aligned to other corresponding isolated complete cardiac cycles in other channels.

The assessment system 110 determines a value (e.g., risk/likelihood, binary indication) indicative of presence of cardiac disease or condition (e.g., coronary arterial disease, pulmonary hypertension, pulmonary arterial hypertension, left heart failure, right-sided heart failure, abnormal left-ventricular end diastolic pressure (LVEDP)) by directly inputting the pre-processed data set to a set of one or more neural networks 232a, 232b (e.g., one or more deep neural networks, one or more convolutional neural networks, etc.), or ensemble(s) thereof, trained with one or more biophysical signal data sets acquired from a plurality of patients labeled with a diagnosis of presence of coronary artery disease (e.g., significant coronary artery disease). In some embodiments, the label for the presence of coronary artery disease comprises a Gensini-based score determined as a combination of a severity-weighted scoring and location-weighted scoring for a coronary lesion diagnosed in the patient's myocardium.

In some embodiments, the neural network(s) 232a (e.g., deep neural network(s), convolutional neural network(s), etc.), or ensemble(s) thereof, receives training data comprising a Gensini score (e.g., a modified Gensini score as described herein) for a patient/subject.

In some embodiments, the neural network(s) 232b (e.g., deep neural network(s), convolutional neural network(s), etc.), or ensemble(s) thereof, receives training data comprising a binary array in which each element is mapped to a coronary artery disease being diagnosed at a given coronary artery. In some embodiments, the array binary array includes mapping to a disease state in coronary artery selected from the group consisting of a left main artery (LMA), a proximal left circumflex artery (Prox LCX), a mid-left circumflex artery (mid LCX), a distal left circumflex artery (Dist LCX), a LPAV, a first obtuse marginal (OM1), a second obtuse marginal (OM2), a third obtuse marginal (OM3), a proximal left anterior descending artery (Prox LAD), a mid-left anterior descending artery (Mid LAD), a distal left anterior descending artery (Dist LAD), a left anterior descending artery (LAD) D1, a left anterior descending artery (LAD)

D2, a proximal right coronary artery (Prox RCA), a mid-right coronary artery (Mid RCA), a distal right coronary artery (Dist RCA), and an acute-marginal branch right of the posterior-descending-artery (AcM R PDA). Other coronary arter(ies) may be included.

Figure 2B:
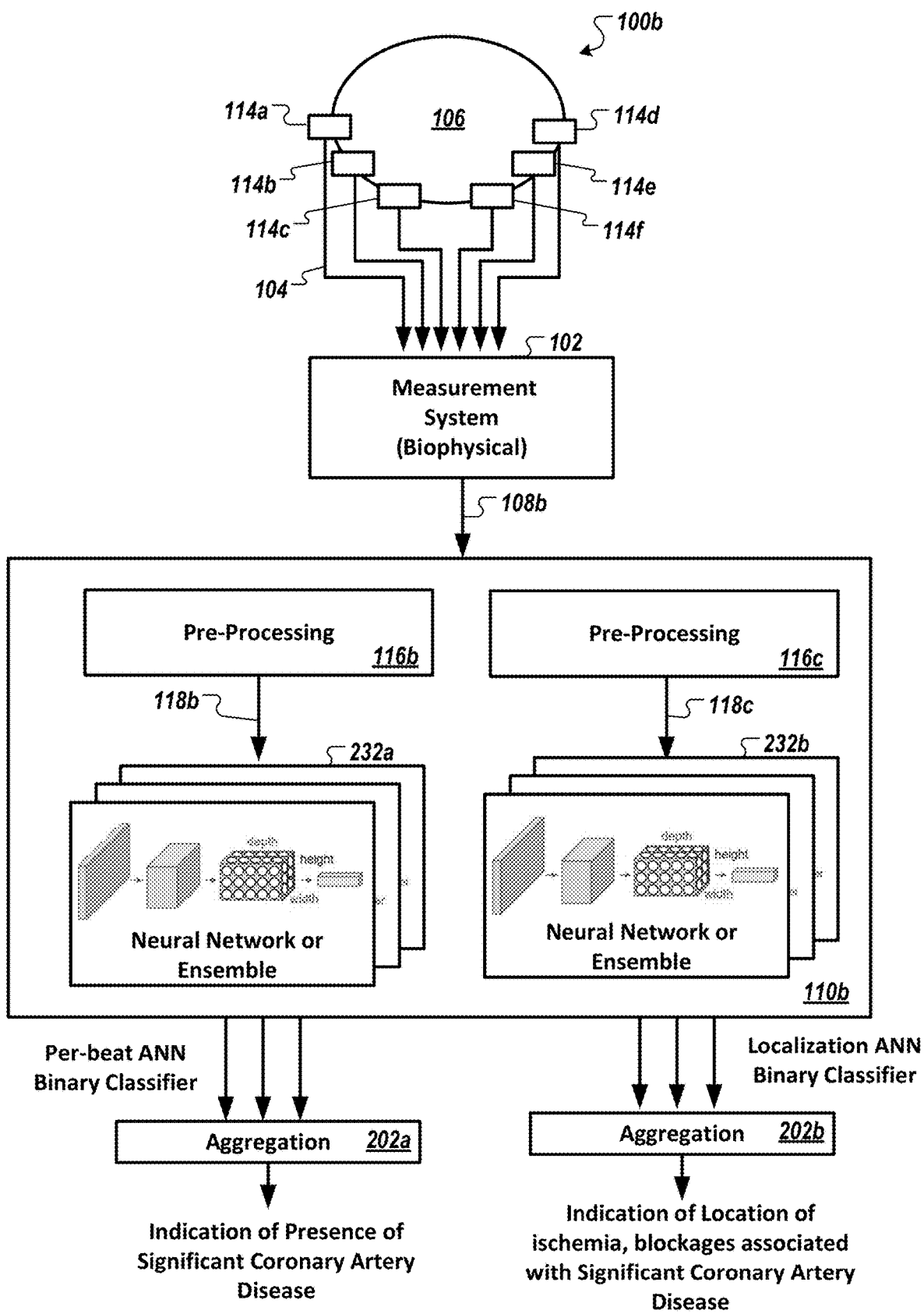
FIG. 2B is a diagram of a system comprising one or more neural networks (e.g., one or more deep neural network(s), one or more convolutional neural network(s), etc.), or ensemble(s) thereof, configured to predict presence/non-presence of coronary artery disease in a coronary artery, in accordance with an illustrative embodiment in the cardiovascular context.

FIG. 2B is a diagram of a system 100b comprising one or more neural networks 232a, 232b (e.g., one or more deep neural networks, one or more convolutional neural networks, etc.), or ensemble(s) thereof, configured to predict presence/location of coronary artery disease in a coronary artery, in accordance with an illustrative embodiment in the cardiovascular context. As shown in FIG. 2B, the non-invasive measurement system 102 acquires a plurality of biophysical signals 104 via measurement probes 114 (shown as probes 114a, 114b, 114c, 114d, 114e, and 114f) from a subject 106 to produce a biophysical data set 108c.

Following acquisition, an assessment system 110b receives the biophysical data set 108b directly, or indirectly over a network or a data repository comprising, e.g., a storage area network, from the measurement system 102.

Assessment system 110b includes, in this embodiment, a separate pre-processing module for each set of the one or more neural networks (e.g., deep neural network(s), convolutional neural network(s), etc.), or ensemble(s) thereof, (shown as pre-processing 116b and 116c). The pre-processing modules 116b, 116c are configured to pre-process the biophysical data set 108b from at least one of the acquisition channels to generate one or more pre-processed data sets (shown as 118b and 118c).

Also, as shown in FIG. 2B, assessment system 110b, in this embodiment, is configured with separate aggregate modules (shown as "Aggregation" modules 202a, 202b) for each of the set of one or more neural networks 232a, 232b (e.g., one or more deep neural networks, one or more convolutional neural networks, etc.), or ensemble(s) thereof.

Figure 2C:
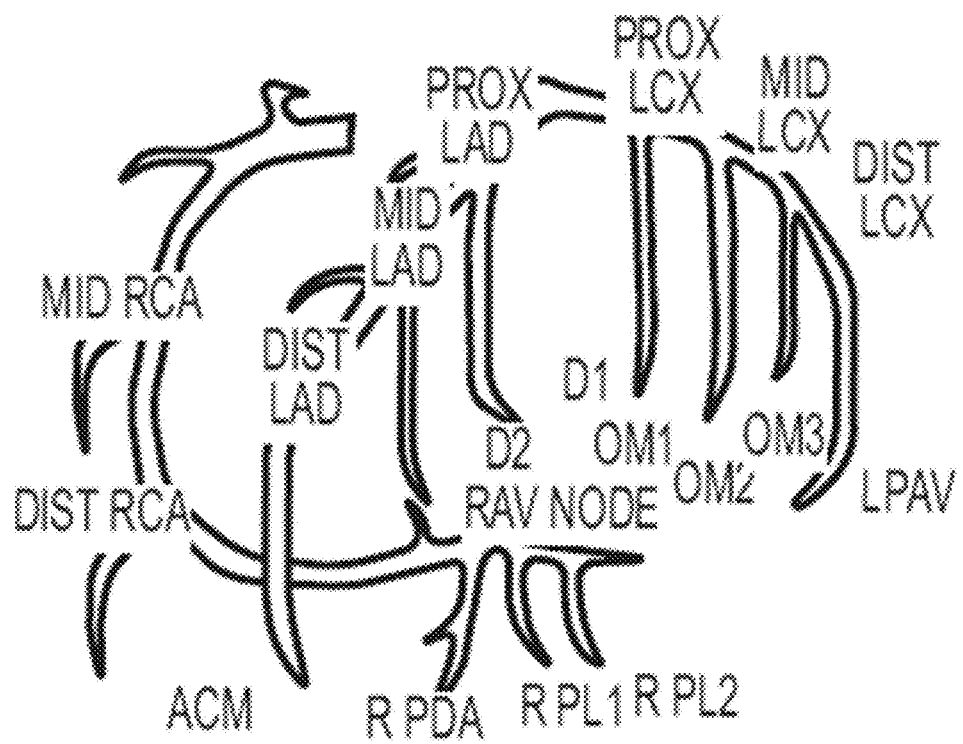
FIG. 2C is a diagram showing coronary arteries that can be classified by the neural network(s) (e.g., deep neural network(s), convolutional neural networks, etc.), or ensemble(s) thereof, of FIGS. 2A and 2B to detect coronary artery disease in accordance with an illustrative embodiment.

FIG. 2C is a diagram showing coronary arteries that can be classified by the neural network (e.g., deep neural network, convolutional neural network, etc.), or ensemble(s) thereof, of FIGS. 2A and 2B to detect coronary artery disease in accordance with an illustrative embodiment. As shown in FIG. 2C, the left main coronary artery supplies blood to the left side of the heart muscle and is divided into two branches: Left Anterior Descending (LAD) Artery and Left Circumflex Artery (LCX). LAD provides blood to the front of the left side of the heart, while the LCX supplies blood to the back and outer side of the heart muscle. RCA supplies blood to the right atrium, right ventricle, and bottom portion of both ventricles and back of the septum. The localization of the Coronary Artery Disease (CAD) is of paramount importance as it will help cardiologists develop a strategy for intervention, medical therapy or both.

Figure 3:
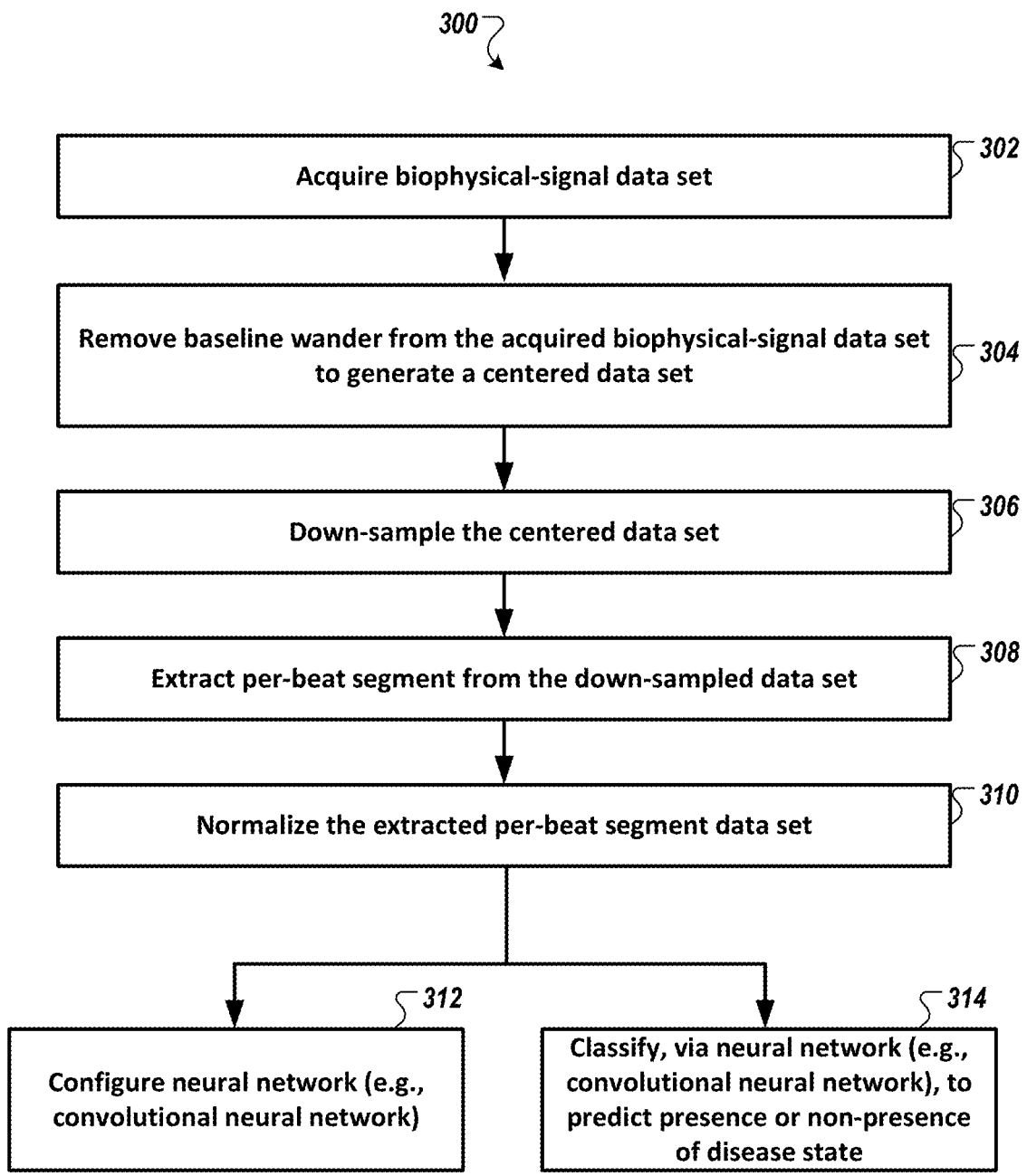
FIG. 3 is a diagram showing a pre-processing operation of FIG. 1, in accordance with an illustrative embodiment.

FIG. 3 is a diagram showing a pre-processing operation of FIG. 1, in accordance with an illustrative embodiment in the cardiovascular context.

The method 300 includes acquiring (shown as step 302) a biophysical-signal data set 108, e.g., from the measurement system 102 or from a data repository having received the biophysical data set from the measurement system 102, e.g., as described in relation to FIG. 1. In some embodiments, six simultaneously sampled signals are captured from a resting subject as a raw differential channel signal data set (e.g., comprising channels that may be called as "ORTH1", "ORTH2", and "ORTH3") in which the signals embed the inter-lead timing and phase information of the acquired signals, specific to the subject. Geometrical contrast arising from the interference in the phase plane of the depolarization wave with the other orthogonal leads can be used which can facilitate superimposition of phase space information on a three-dimensional representation of the heart. Noiseless subspaces further facilitate the observation of the phase of these waves. That is, the phase of the orthogonal leads carries the information about the structure and generates geometrical contrast in the image. Phase-contrast takes advantage of the fact that different bioelectric structures have different impedances, and so spectral and non-spectral conduction delays and bends the trajectory of phase space orbit through the heart by different amounts. In the cardiovascular context, these small changes in trajectory can be normalized and quantified beat to beat and corrected for abnormal or poor lead placement, and the normalized phase space integrals can be mapped to a geometric mesh for visualization.

In some embodiments, the non-invasive measurement system 102 is configured to sample a biophysical signal (e.g., bipolar biopotential signals) at about a sampling rate greater than 1 kHz (e.g., 8 kHz) for each of three differential channels orthogonally placed on a subject for a duration between about 30 and about 1400 seconds, e.g., for about 210 seconds. Other duration and sampling rate may be used.

The assessment system 110 then, in some embodiments, removes at step 304 the baseline from the acquire draw signal. The baseline wander removal operation is implemented, in some embodiments, as a phase-linear $2^{nd}$ order high-pass filter (e.g., a second-order forward-reverse high-pass filter having a cut-off frequency at 0.67 Hz). The forward and reverse operation ensures that the resulting pre-processed biophysical-signal data set is phase-linear. Other phase-linear operations be used—e.g., based on wavelet filters, etc.

In other embodiments, a multi-stage moving average filter (median filter, e.g., with an order of 1500 milliseconds, smoothed with a 1-Hz low-pass filter) is used to extract a bias signal from each of the input raw differential channel signals. The bias is then removed from the signals by subtracting estimations of the signals using maximums of probability densities calculated with a kernel smoothing function.

In some embodiments, the signal is run though a signal quality test where the relevant output is the time-indices of the signal appropriate (of sufficient quality) for analysis. An example of the signal-quality test is described in U.S. Provisional Appl. No. 62/784,962, titled "Method and System for Automated Quantification of Signal Quality," which is concurrently filed herewith and incorporated by reference herein in its entirety.

In some embodiments, assessment system 110 downsamples at step 306 the input signal or the pre-processed signal (e.g., to 1 kHz). In some embodiments, the downsampling operation is an averaging operator or a decimation operator.

In some embodiments, the method further includes normalizing the input acquired biophysical signal data set 108 or the pre-processed signal 118. Similar types of downsampling, baseline wander, and/or normalization operation can be applied to other biophysical-signal data sets.

In some embodiments, the method includes using only a portion of the acquired biophysical signal data set, e.g., after a pre-defined time or data set offset (e.g., after the first 31 seconds). It is observed, in some embodiments, that such operations can minimize and/or reduce motion artifacts (and therefore improve signal quality) that can be introduced by movement of a subject during the start of a measurement acquisition. It is also observed that such operations can minimize and/or reduce distortions (and therefore improve signal quality) in the measurement that can be attributed to probe placement and contacts and which is generally observed to reduce over the course of the measurement acquisition as the probe settles. Other time or data set offset techniques can be used; e.g., those based on quantification of noise in the acquired biophysical data set which may be the result of or associated with the biophysical signal acquisition protocol (instructions), types of probes or electrodes used, and the types and/or configurations of components such as cables for the transmission of signals, the biophysical signal measurement system, the biophysical signal acquisition space/environment, proximity to other medical equipment, etc.

Assessment system 110, in some embodiments, extracts at step 308 on a per-beat basis a plurality of "clean" sub-signals from the acquired-biophysical-signal data set (or other intermediary signals, as, e.g., discussed herein).

Figure 4:
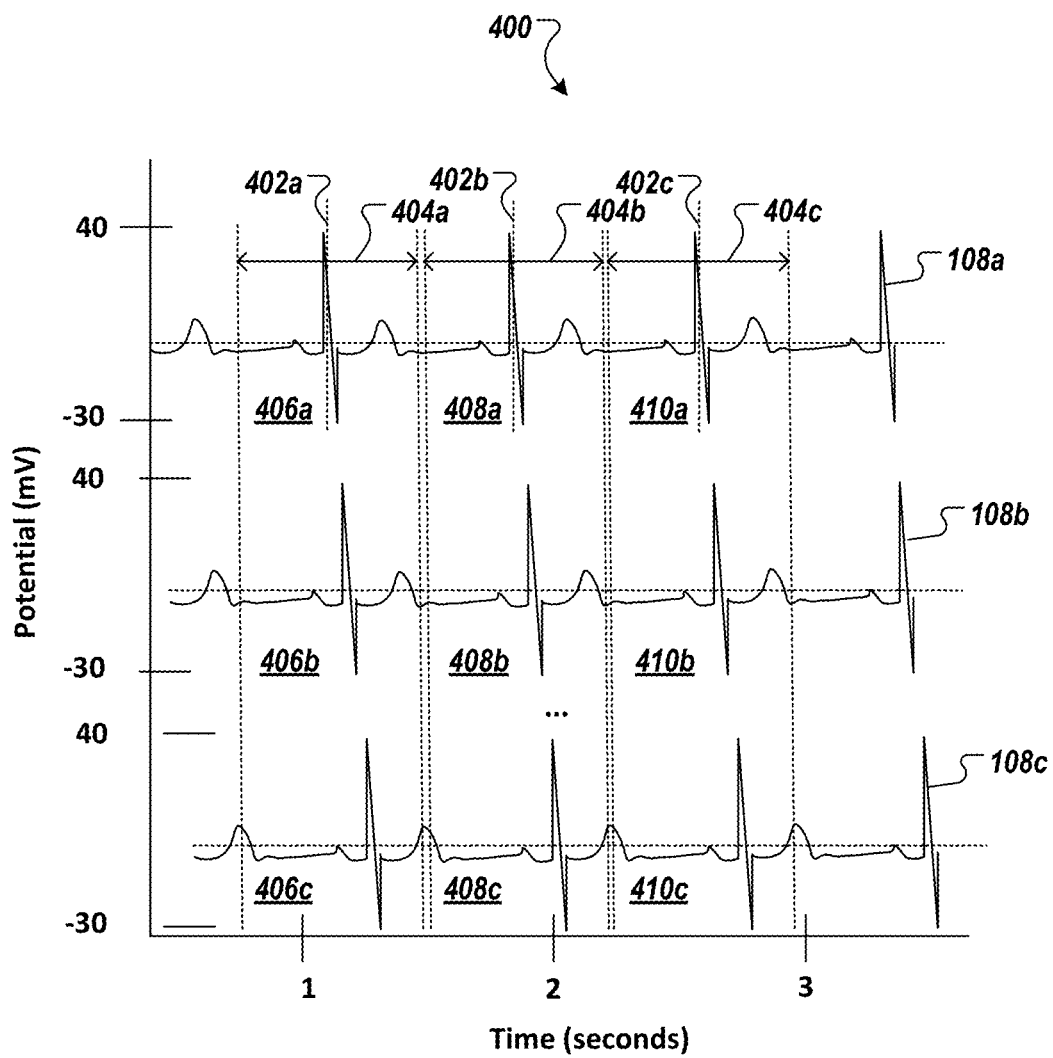
FIG. 4 is a diagram showing a beat-to-beat isolation of a biophysical-signal data set of FIG. 3, in accordance with an illustrative embodiment in the cardiovascular context.

FIG. 4 is a diagram showing a beat-to-beat isolation of FIG. 3, in accordance with an illustrative embodiment. As shown in FIG. 4, assessment system 110 detects the maximum peaks (shown as 402a, 402b, 402c) in the acquired biophysical-signal data set 108 (or an intermediary data set derived from the biophysical-signal data set such as the down-sampled signal data set) then isolates each beat as a data set defined in a fixed window (shown as 404a, 404b, 404c) placed around the maximum peak (108a, 108b, 108c) with the peak at the center of the window. In some embodiments, assessment system 110a employs the Pan-Tompkins algorithm as described in Pan and Tompkins, "A Real-Time QRS Detection Algorithm," IEEE Trans. Biomed. Eng., Vol. 32, No. 3, (March 1985), the entirety of which is hereby incorporated by reference herein, to detect peaks (402a, 402b, 402c) in the down-sampled signal data set (108a, 108b, 108c). In some embodiments, assessment system 110 generates a fixed-window of about 0.75 second, which corresponds to a heart rate of 80 beats per second. Other window sizes and centering techniques maybe used.

In some embodiments, to preserve the phase-gradient information among the acquired biophysical data set (or the intermediary dataset being processed in the assessment analysis), assessment system 110 applies the same time window (e.g., 404a, 404b, 404c) as obtained in the peak detection of the first channel (e.g., ORTH1) to extract the beats from one or more of the other channels (e.g., ORTH2 and ORTH3). As shown, assessment system 110 generates a first beat-to-beat segment from channel "1" (406a) (also referred to as channel "ORTH1") that are phase aligned with both a beat-to-beat segment from channel "2" (406b) (also referred to as channel "ORTH2") and a beat-to-beat segment from channel "3" (406c) (also referred to as channel "ORTH3"), which can be used collectively as one input to the convolutional neural network. A second set of inputs are shown as a beat-to-beat segment from channel "1" (408a), a beat-to-beat segment from channel "2" (408b), and a beat-to-beat segment from channel "3" (408c). A third set of inputs are shown as a beat-to-beat segment from channel "1" (410a), a beat-to-beat segment from channel "2" (410b), and a beat-to-beat segment from channel "3" (410c). Indeed, output(s) of the Pre-Processing module 116 to be provided as the input(s) to the one or more neural networks (e.g., deep neural network such as convolutional neural networks, etc.), or ensemble(s) thereof, is a set of data segments (comprising a single complete cardiac cycle) from a phased-aligned time window (e.g., a 0.75-second window) from each, or a portion, of the acquisition channels. In some embodiments, all data segments extracted from the Pre-Processing module 116 are provided as input to the neural network(s) 132 (e.g., to the deep neural network(s), to the convolutional neural network(s), etc.), or ensemble(s) thereof (e.g., for training or analysis). In other embodiment, data segments extracted from some, but not all, of the acquisition channels are provided to the neural network(s) 132 (e.g., deep neural network(s), convolutional neural network(s), etc.), or ensemble(s) thereof (e.g., for training or analysis). In yet other embodiments, data segments extracted from some, but not all, of a given acquisition channel are provided to the neural network(s) 132 (e.g., deep neural network(s), convolutional neural network(s), etc.), or ensemble(s) thereof.

Referring back to FIG. 3, following the extraction of the beat-to-beat segments, assessment system 110 is configured to normalize at step 310 each of the beat-to-beat segments as inputs to the neural network (e.g., deep neural network, convolutional neural network, etc.), or ensemble(s) thereof. In some embodiments, the assessment system 110 is configured to scale each beat on each channel per Equation 1:

$$\left(0.5 * \left(\frac{Signal_{input}}{\max(|Signal_{input}|)} + 1\right)\right) - \mathrm{mean}(Signal_{input}) + 0.5 \quad \text{(Equation 1)}$$

As shown, the system divides each channel by its maximum absolute value in the window to provide a data set that is bounded by the range of −1 and +1. Assessment system 110 then adds 1 to the result and divide by 2 to provide a signal that is bounded within 0 and 1. Assessment system 110 then subtracts the result by a mean of the windowed data set and then add 0.5 to provide a signal data set with a mean of 0.5 bounded between 0 and 1. The same is performed for the other channel(s) to provide a similar range and mean for all the training examples, helping the network learn and generalize better. Other normalization operation may be used.

Referring still to FIG. 3, assessment system 110 is configured to then input the normalized beat-to-beat data set to a neural network 132 (e.g., a deep neural network, a convolutional neural network, etc.), or an ensemble(s) thereof). The system may apply the normalized beat-to-beat data set to train, at step 312, the neural network 132 (e.g., deep neural network, convolutional neural network, etc.), or ensemble(s) thereof. The system may alternatively apply the normalized beat-to-beat data set to be classified, at step 314, by the trained neural network (e.g., trained deep neural network, trained convolutional neural network, etc.), or trained ensemble(s), to predict the presence or non-presence of a disease state or condition (e.g., presence or non-presence of coronary artery disease or other condition) in a patient and/or presence/location of disease or condition in a coronary artery.

In some embodiments, assessment system 110 is configured with more than one neural networks 132a, 132b (e.g., deep neural networks, convolutional neural networks, etc.), or ensemble(s) thereof. Each of the neural networks 132a, 132b (e.g., deep neural networks, convolutional neural networks, etc.), or ensemble(s) thereof, may receive the normalized beat-to-beat data sets and generate a set of predictors that are combined (e.g., via an aggregation operator 202 as shown in FIG. 2A; or via operators 202a, 202b as shown in FIG. 2B).

Method of Optimization/Training of Convolutional Neural Network

Figure 5:
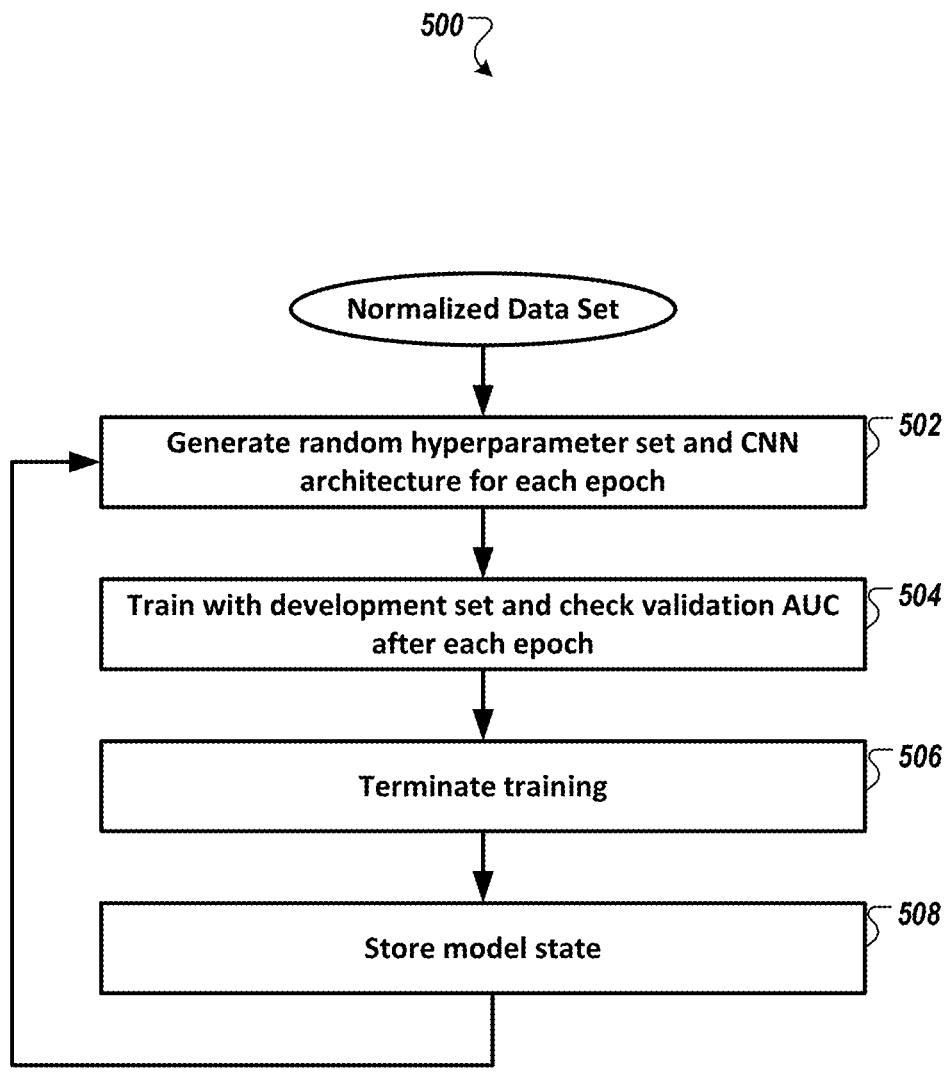
FIG. 5 is a diagram showing a method of training of the neural network(s) (e.g., deep neural network(s), convolutional neural network(s), etc.), or ensemble(s) thereof, of FIG. 1, in accordance with an illustrative embodiment.

FIG. 5 is a diagram showing a method 500 of training of a neural network (e.g., a deep neural network, a convolutional neural network, etc.), (e.g., 132a, 132b, 232a, 232b), or ensemble(s) thereof, in accordance with an illustrative embodiment. In FIG. 5, the normalized data set as provided from the pre-processing processing of FIG. 3 is provided as the input to the training stage. In the training stage, a set of randomly generated neural network configurations (e.g., generated deep neural network configurations, generated convolutional neural network configurations, etc.), or ensemble(s) thereof, is trained with a development set of biophysical-signal data (e.g., phase gradient biophysical-signal data, wide-band phase gradient biophysical-signal data) as normalized and pre-processed per the steps discussed in relation to FIG. 3 and evaluated with a validation set of phase-gradient biophysical signal data sets. Assessment system 110, in some embodiments, is configured to used Gensini-based scoring as part of the input to the randomly generated neural networks (e.g., randomly generated deep neural networks, randomly generated convolutional neural networks, etc.), or ensemble(s) thereof.

In some embodiments, assessment system 110 assigns a single Gensini-based score to a subject (i.e., to an acquired wide-band phase-gradient data set, and normalized data set derived from the acquired wide-band phase-gradient data set) that reflects the total burden on the myocardium as caused by their coronary lesions, which are localized and quantified by coronary angiography. In some embodiments, the Gensini-based score is based on Equation 2 as described in Goffredo G. Gensini, "Coronary arteriography," Futura Pub. Co (1975), which is incorporated by reference herein in its entirety:

$$\text{Gensini\_score} = \Sigma_i \text{Severity}_i \times \text{Location}_i \quad \text{(Equation 2)}$$

In Equation 2, i is the number of identified coronary lesions, $\text{severity}_i$ is a severity weight of values $\{1, 2, 4, 8, 16, \text{ or } 32\}$ for an evaluated reduction of diameter of 25%, 50%, 70%, 90%, 99%, and 100% for each coronary lesion i, and $\text{location}_i$ is a location weight of $\{5 \ldots 0.5\}$ that is defined to a location depending on its relative impact, to other locations, to overall coronary circulation. Indeed, if the lesion is more upstream in the coronary circulation pathway (e.g., proximal to the aorta), then that lesion affects circulation to a greater degree than a lesion that is quite low (distal) in the circulation. The location score in an example ranges from 5 to 0.5 in which a value of 5.0 is assigned to a location that most impacts the circulation and a value of 0.5 is assigned to a location that has the least impact (e.g., according to the Gensini scale). Other scoring values may be used.

In some embodiments, assessment system 110 assigns a modified Gensini-based score to a subject (i.e., to an acquired phase-gradient biophysical data set, an acquired wide-band phase gradient biophysical-signal data set), or a normalized data set derived therefrom, that reflects a burden as caused by a worst coronary lesion as localized and quantified by coronary angiography, per Equation 3:

$$\text{Gensini\_score} = \text{select\_max}(\text{Severity}_i \times \text{Location}_i) \quad \text{(Equation 3)}$$

Indeed, as provided in Equation 3, the system only considers only the worst-case lesion, i.e., the lesion with the maximal value of severity weight multiplied by the location weight.

Referring still to FIG. 5, for each data preparation and learning step (referred to as an epoch), assessment system 110 executes a pass through all of the training data set and calculates an AUC score from a validation data set. Because a single phase-gradient biophysical data set (e.g., wide-band phase gradient biophysical signal data set) can be segmented into a plurality of windowed data sets, the system, in some embodiments, is configured to combine all, or a substantial portion of, predictions on the plurality of patient's heart beats via a mean operator to provide the combined AUC score. Assessment system 110 may perform the learning and evaluating steps in a loop that can be run across multiple machines simultaneously without synchronization.

In some embodiments, assessment system 110 is configured to sample the data set in a stratified manner so to have a similar ratio of CAD-positive data sets and CAD-negative data sets in both the training data sets and the validation sets.

Referring still to FIG. 5, assessment system 110 is configured to generate a random set of hyperparameters and a neural-network architecture (e.g., deep-neural network architecture, convolutional neural network architecture, etc.) from a set of candidates as provided in Table 1, which shows an example hyperparameter search space for a beat-to-beat neural-network-based analysis (e.g., deep-neural network-based analysis, CNN-based analysis, etc.).

TABLE 1

| Hyperparameter | Candidate values |
| --- | --- |
| batch size | $\{16, 32, 64, 128, 256, 512\}$ |
| learning rate | $[10^{-5}, 10^{-3}]$ |
| # convolutional layers | $\{1, 2, 3, 4\}$ |
| filter size | $\{3, 4, 5, \ldots, 49, 50\}$ |
| # filters in first convolutional layer | $\{2, 4, 8, 16\}$ |
| increase in # filters in subsequent layers | $\{\text{'x1'}, \text{'x2'}\}$ |
| # additional dense layers | $\{0, 1, 2, 3\}$ |
| size of additional dense layers | $\{10, 25, 50, 100, 200, 500, 1000\}$, with layer $i \geq$ layer $i + 1$ |
| activation function | $\{\text{'elu'}, \text{'softsign'}\}$ |
| target | $\{\text{'CAD'}, \text{'log max gensini'}\}$ |
| input frequency | $\{100 \text{ Hz}, 250 \text{ Hz}, 500 \text{ Hz}, 1000 \text{ Hz}\}$ |
| dilation rate | $\{1, 2, 3, 4\}$ |
| size of max pooling | $\{3, 5, 7, 9, 11, 13, 15, 17, 19, 21, 23, 25, 27, 30\}$ |
| dropout | 0.5 |
| final layer activation function | 'sigmoid' |
| loss function | 'mean_squared_logarithmic_error' |
| optimizer | 'Adam' |

Indeed, assessment system 110 is configured to generate a plurality of hyperparameter sets for a template neural network (e.g., template deep neural network, template convolutional neural network, etc.), or ensemble(s) thereof, in which each of the plurality of hyperparameter sets is generated by a random, or pseudo-random selection, from a set of hyperparameters (e.g., batch size, learning rate, convolutional layer, filter size, a number of filter in a first convolutional layer, an increase in filter in subsequent layer, number of additional dense layers, size of additional dense layers, activation function type, target, dilation rate, dropout, etc.). In some embodiments, assessment system 110 is configured to optimize the neural network (e.g., deep neural network, convolutional neural network, etc.), or ensemble(s) thereof, via Bayesian hyperparameter optimization.

Table 2 shows a set of hyperparameter search space categories and candidate values for neural network-based coronary artery disease localization analysis (e.g., deep-neural network-based coronary artery disease localization analysis, CNN-based coronary artery disease localization analysis). Other hyperparameter search space categories and respective candidate values may be employed that are within the spirit and equivalence of the Tables 1 and 2. In Tables 1 and 2, assessment system 110, in some embodiments, uses a single element from a set defined in "{ }", and assessment system 110 uses a value in the range "[ ]".

TABLE 2

| Hyperparameter | Candidate values |
| --- | --- |
| batch size | {64, 128, 256, 512, 1024, 2048} |
| learning rate | [$10^{-5}$, $10^{-3}$] |
| # convolutional layers | {1, 2, 3, 4} |
| first convolutional layer filter size | {13, 15, 17, 19, 21} |
| # filters in first convolutional layer | {4, 6, 8, 10, 12, 14, 16} |
| stride | {1, 3, 5} |
| # additional dense layers | {0, 1, 2} |
| size of additional dense layers | {10, 50}, with layer i ≥ layer i + 1 |
| activation function | {'tanh', 'relu'} |
| target | {['LAD', 'LCX', 'RCA]} |
| input frequency | {1000 Hz} |
| size of max pooling | {1, 2, 3} |
| dropout | [0, 0.7] |
| loss function | {'mean_squared_logarithmic_error', 'mean_squared_error', 'mae'} |
| optimizer | {'Adam'} |
| input channels | {ORTH1, ORTH2, ORTH3} |

Figure 6:
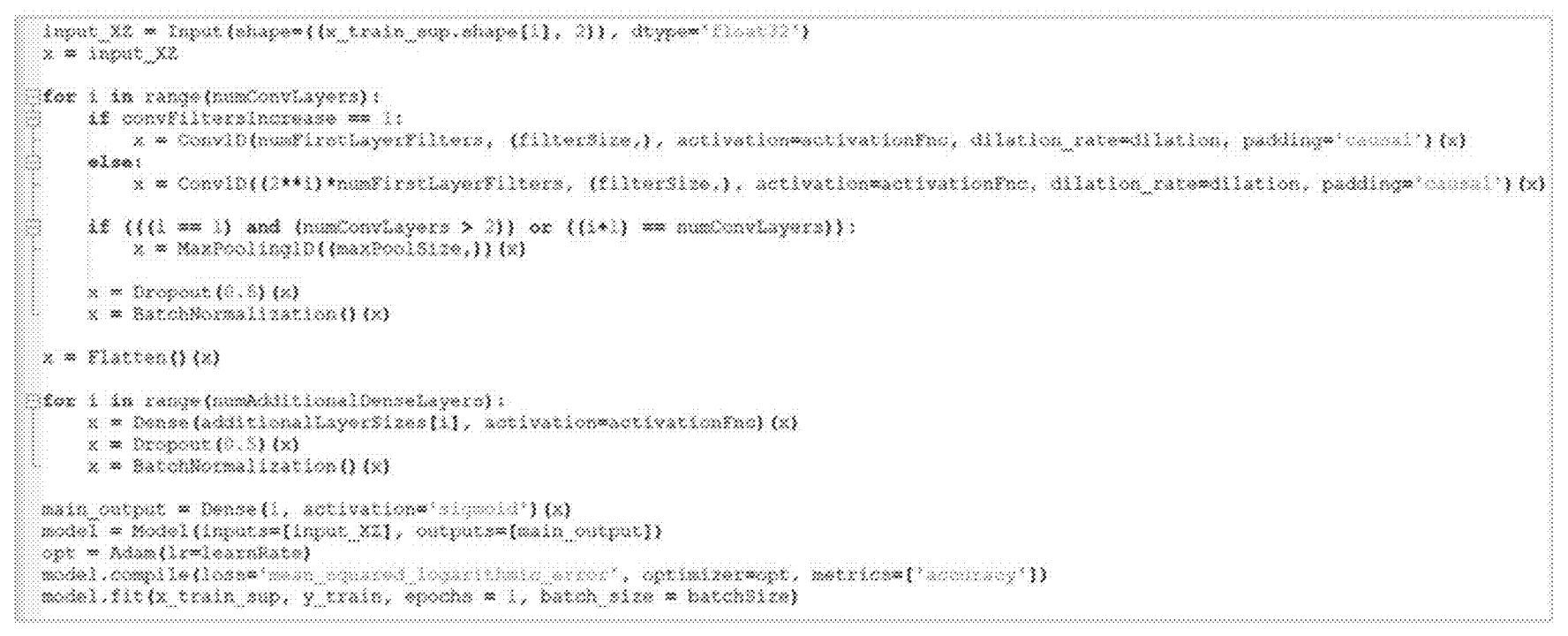

FIG. 6 shows executable code to construct the neural network model (e.g., deep neural network model, convolutional neural network model, etc.) from a set of randomly selected hyperparameters in accordance with an illustrative embodiment. The executable code of FIG. 6 are configured for operation in Keras open-source neural network library and are shown in Python. Example of random-based searching for hyperparameter optimization is described in Bergstra and Yoshua, "Random search for hyper-parameter optimization," Journal of Machine Learning Research 13, 281-305, (February 2012), which is incorporated by reference herein in its entirety.

Referring to FIG. 5, assessment system 110 trains at step 504 a set of neural network models (e.g., deep neural network, convolutional neural networks, etc.), or ensemble(s) thereof, over several epochs in which each epoch include a single pass through the entire training set. At the end of each epoch, assessment system 110 calculates a set of training and validation AUC score. Assessment system 110 selects, in some embodiments, the minimum value of the calculated AUC as the score of the epoch as the worst-case performance to underestimate, rather than overestimate, predictive performance of the neural network model (e.g., deep neural network, convolutional neural network, etc.), or ensembles thereof, under study.

Indeed, assessment system 110 is configured to (i) train, for each of plurality of hyperparameter sets, the template neural network (e.g., template deep neural network, template convolutional neural network, etc.) in which in each instance of the evaluation, the template neural network (e.g., template deep neural network, template convolutional neural network, etc.) is configured with a hyperparameter set of the plurality of hyperparameter sets and (ii) evaluate, for each of plurality of hyperparameter sets, the trained neural network (e.g., deep neural network, convolutional neural network, etc.), or ensemble(s) thereof, with a first validation data set, wherein each evaluation generates an AUC score (e.g., true-AUC score). In some embodiments, the evaluation of the trained neural network 116 (e.g., trained deep neural network, trained convolutional neural network, etc.), or ensemble(s) thereof, may include generating one or more of an accuracy score, a weighted accuracy score, a positive predictive score, a negative predictive score, a F-score, a sensitivity score, a specificity score, and/or a diagnostic odds ratio score. To this end, assessment system 110 is configured to determine a value (e.g., risk/likelihood, binary indication) indicative of presence of cardiac disease or condition (e.g., coronary arterial disease, pulmonary hypertension, pulmonary arterial hypertension, left heart failure, right-sided heart failure, abnormal left-ventricular end diastolic pressure (LVEDP)) by directly inputting the pre-processed data set to a set of one or more neural network(s) (e.g., a set of one or more deep neural network(s), a set of one or more convolutional neural network(s), etc.), or ensemble(s) thereof, trained with one or more biophysical signal data sets acquired from a plurality of patients labeled with a diagnosis of presence of significant coronary artery disease in which the label includes a Gensini-based score determined as a combination of a severity weighted scoring and location weighted scoring for a coronary lesion diagnosed in a region of the myocardium or a particular coronary artery (e.g., from a set of coronary arteries).

Assessment system 110 is configured to determine at step 506 for each epoch whether to stop execution of the training and search loop. The criteria for the stop, in some embodiments, includes whether a predefined number of epochs have been executed (e.g., 10) in which no better high score is observed. At the end of a run, the best scoring model is saved along with the chosen parameters and various outputs such as predictions on the verification set. The algorithm then proceeds to the next run with new, different parameters and CNN architectures.

In some embodiments, prior to applying a data set to the training operation, assessment system 110 is configured to evaluate and reject signals with excessive powerline noise, high-frequency noise, and/or cycle variability noise. In some embodiments, assessment system 110 is configured to perform a signal quality tests to determine whether the wideband phase-gradient signal has sufficient signal quality for subsequent analysis.

True-AUC Scoring

In some embodiments, to provide an improved assessment of the prediction (i.e., classification) algorithm, assessment system 110 is configured to account for the cost of errors and balance of the targeted class in the determination of an AUC score. Factors that can be used include known statistics, performance goals, and measures (e.g., cost of false positive, cost of false negative).

For example, if the system predicts a patient as having coronary artery disease, the subject will likely be subject to further investigation—and thus the cost of a false positive is "low", in terms of patient safety and health, as the further investigation will confirm whether or not the disease is present. On the other hand, if the system predicts a patient as not having the disease when he or she actually does, then the subject will likely not take further action with respect to this diagnosis and thus the cost of a false negative is "high" as patient safety and health may be compromised. Indeed, a false negative will have more cost (again, in terms of patient safety and health) to the patient and clinical team than a false positive and thus the instance of a false negative should in this context be assigned a greater weight (e.g., the cost of false negative is twice the cost of a false positive).

The system, in some embodiments, is configured to generate a modified receiver operator characteristic (ROC) plot that does not include an AUC (area under the ROC curve) measure. AUC curve generally assumes an interest in all possible points along a classifier's ROC curve.

In some embodiments, as an alternatively to AUC measure, the system is configured to use a 1:1 cost. In such embodiment, the system may consider that for every incremental true positive (or decrement in false negatives), an incremental false positive is acceptable. For example, beginning at the bottom-left of a ROC graph, the system may cause an increment of one true positive and one false positive as "1" (along the y-axis) and the false positive rate (along the x-axis) to increase by a fraction of "1" (e.g., $\frac{1}{15}$) due to a class imbalance. Indeed, by traversing a line with a slope emanating from the bottom left of the ROC graph, the system can maintain the requisite balance for a 1:1 cost.

In some embodiments, as an alternatively to AUC measure, the system is configured to use a 1:2 cost ratio for true positives to false positives. In such embodiment, the system may maintain a slope of 7.5 (e.g., as a boundary to maintain the 1:2 cost ratio). The combined line may be referred to as a "class-by-cost" ratio line. Indeed, a suitable classifier may be considered as having a ROC curve with points that is at or above the class-by-cost ratio line. Other ratio values may be set depending on above-noted factors, such as statistics, performance goals, and measures (e.g., cost of false positive, cost of false negative).

Development, Verification, and Gating Data Set

Figure 7:
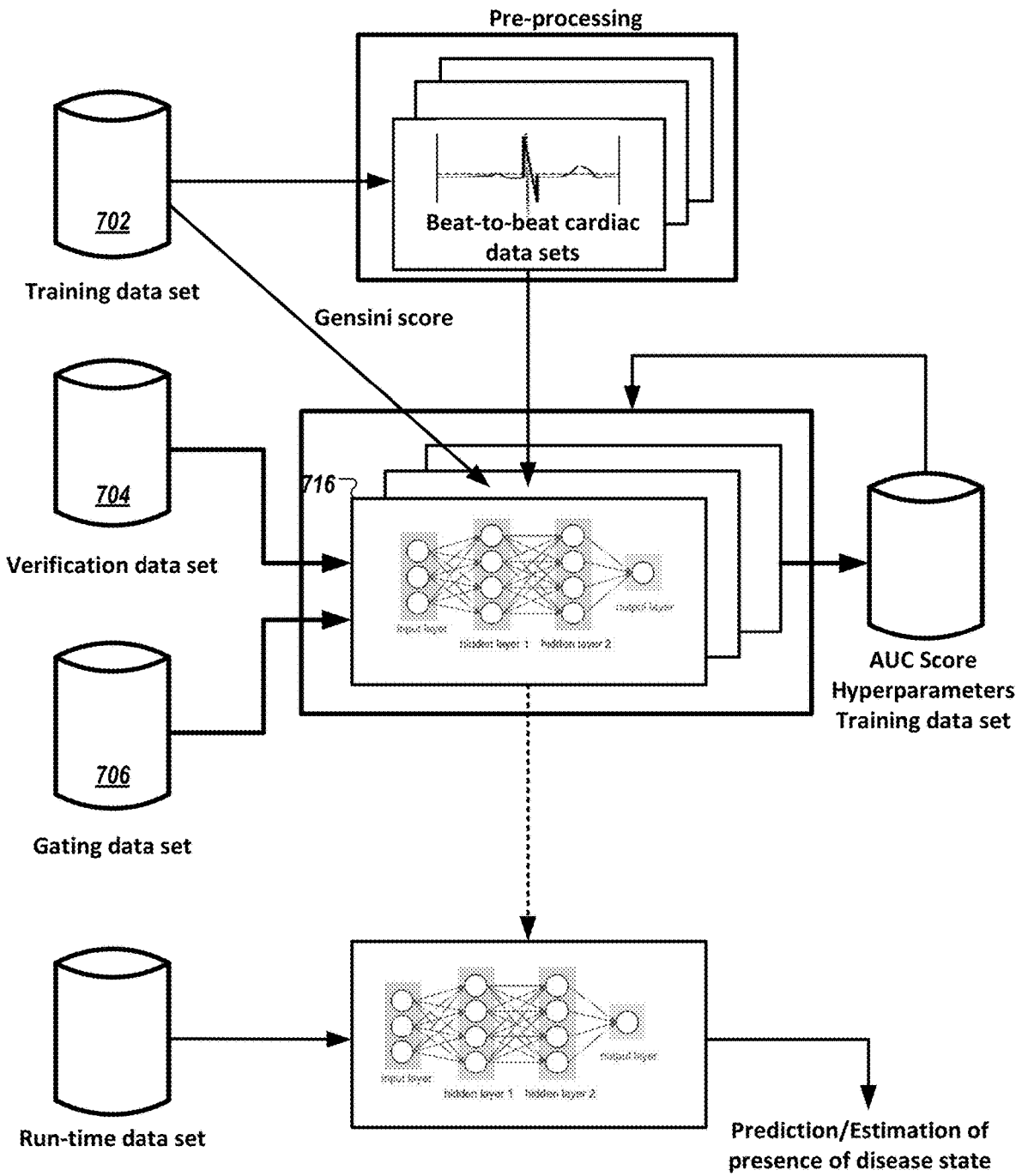
FIG. 7 is a diagram showing use of development, verification, and gating data sets to construct the neural network model (e.g., deep neural network model, convolutional neural network model, etc.), or ensemble(s) thereof, of FIG. 6 in accordance with an illustrative embodiment.

FIG. 7 is a diagram showing use of development, verification, and gating data sets to construct the convolutional neural network model of FIG. 6 in accordance with an illustrative embodiment. As shown in FIG. 7, a first set of phase-gradient data sets (e.g., wide-band phase gradient biophysical data sets) is used for a training data set (shown as "Training data set" 702); a second set of phase-gradient data sets e.g., wide-band phase gradient biophysical data sets) is used for a verification data set (shown as "Verification data set" 704); and a third set of phase-gradient data sets e.g., wide-band phase gradient biophysical data sets) is used for a gating data set (shown as "Gating data set" 706). The data sets 702, 704, 706 provide for different tiers of testing. The training data set, in some embodiments, is constantly tested to optimize and train the neural network (e.g., deep neural network, convolutional neural network, etc.). The verification dataset is a withheld set that is only occasionally evaluated to confirm performance of a trained neutral network (e.g., trained deep neural network, trained convolutional neural network, etc.). The gating data set is used to gate, i.e., move a trained neural network (e.g., a trained deep neural network, a trained convolutional neural network, etc.) into a final/locked configuration. Gating, for example, may only be assessed once or twice.

Each of the phase-gradient data sets (702, 704, and 706) is evaluated by coronary angiography in some embodiments to localize and quantify the subject's coronary lesion(s). Each of the phase-gradient data sets (702, 704, and 706) is pre-processed as described in relation to FIG. 3 to produce beat-to-beat cardiac data sets.

Wide-Band Phase-Gradient Cardiac Biophysical Data Set

Figures 8A, 8B:
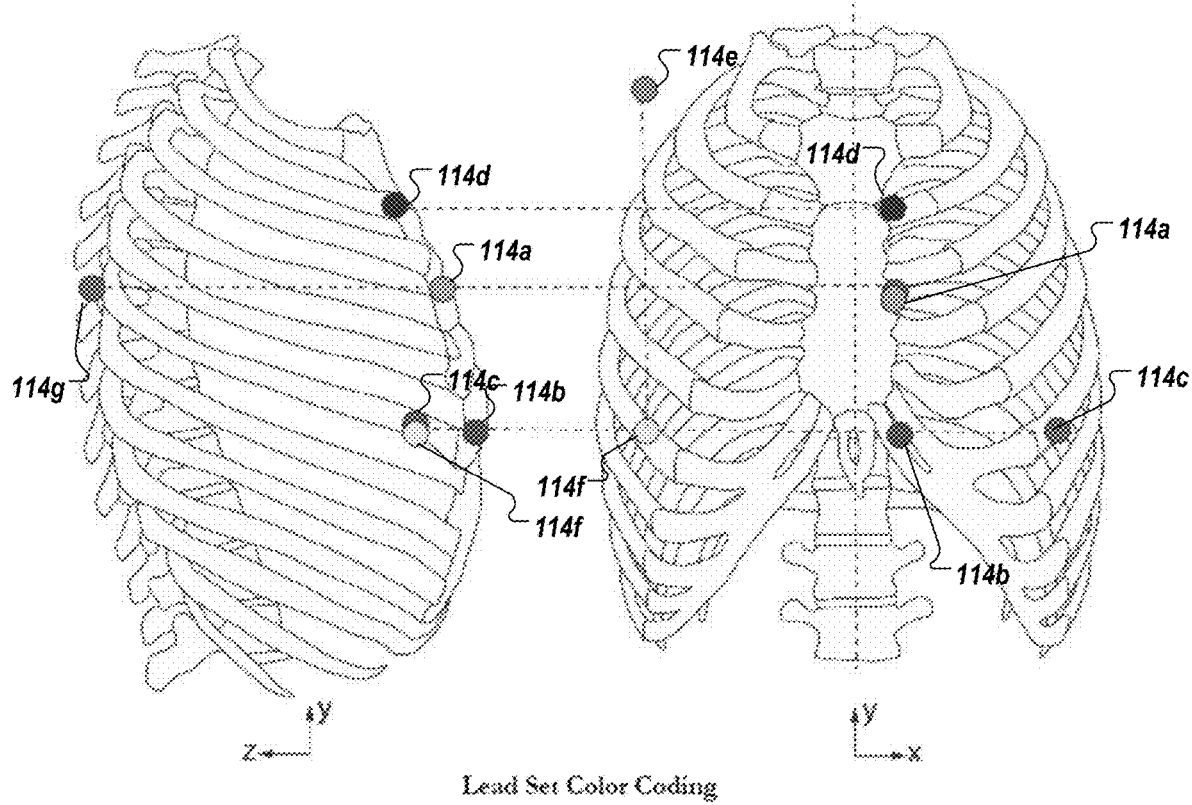
FIG. 8A shows a side view of placement of surface electrodes or probes to the chest and back of a subject or patient, in accordance with an illustrative embodiment.
FIG. 8B shows a front view of placement of the surface electrodes or probes to the same patient, in accordance with an illustrative embodiment.

FIGS. 8A and 8B are diagrams showing an example placement of surface electrodes as probes 114a-114f at the chest and back of a patient or subject to acquire biopotential signals associated with cardiac signal data set, in accordance with an illustrative embodiment. FIG. 8A shows a side view of placement of the surface electrodes 114a-114g to the chest and back of the patient, in accordance with an illustrative embodiment. FIG. 8B shows a front view of placement of the surface electrodes 106a-106g to the same, in accordance with an illustrative embodiment. As shown, the surface electrodes are positioned at (i) a first location proximal to a right anterior axillary line of the subject corresponding to a 5th intercostal space; (ii) a second location proximal to a left anterior axillary line corresponding to the 5th intercostal space; (iii) a third location proximal to a left sternal border corresponding to a 1st intercostal space; (iv) a fourth location proximal to the left sternal border below the patient's sternum and lateral to a xiphoid process; (v) a fifth location proximal to the Left sternal border corresponding to a 3rd intercostal space; (vi) a sixth location proximal to a back directly opposite of the fifth location and left of the patient's spine; and (viii) a seventh location proximal to a right upper quadrant of the patient corresponding to a 2nd intercostal space along a left axillary line.

Experimental Results

CADLAD Study. A "Coronary Artery Disease—Learning Algorithm Development" (CADLAD) study was untaken that involves two distinct stages to support the development and testing of the machine-learned algorithms.

In stage 1 of the CADLAD study, paired clinical data were used to guide the design and development of the pre-processing, feature extraction, and machine learning phase of the development. That is, the collected clinical study data were split into three cohorts: a training cohort (50%), a validation cohort (25%), and a verification cohort (25%). Similar to the steps described above for processing signals from a patient for analysis, each acquired data set was first pre-processed to clean and normalize the data. Following the pre-processing processes, a set of features were extracted from the signals in which each set of features was paired with a representation of the true condition—for example, the binary classification of the presence or absence of significant CAD or the scored classification of the presence of significant CAD in a given coronary artery. The final output of stage 1 was a fixed algorithm embodied within a measurement system.

In stage 2 of the CADLAD study, the machine-learned algorithms were used to provide a determination of significant CAD against a pool of previously untested clinical data (namely, a verification dataset). The criteria for disease were established as that defined in the American College of Cardiology (ACC) clinical guidelines, specifically as that greater than 70% stenosis by angiography or less than 0.80 fraction-flow by flow wire.

In another aspect of the CADLAD study, an assessment system was developed that automatically and iteratively explores combinations of features in various functional permutations with the aim of finding those combinations which can successfully match a prediction based on the features. To avoid overfitting of the solutions to the training data, the validation sets were used as a comparator. Once candidate predictors have been developed, they are then manually applied to a verification data set to assess the predictor performance against data that has not been used at all to generate the predictor.

Beat-to-Beat Convolutional Neural Network. Experiments conducted from the data acquired from the CADLAD study shows that the exemplary system (e.g., 110, 110a, 110b) can detect significant coronary artery disease (CAD) via a neural network (e.g., convolutional neural network (CNN)) that is trained with beat-to-beat segmented data from wide-band phase gradient biopotential signal data sets. The wide-band phase-gradient biopotential data sets were only pre-processed to remove baseline wander, normalize the data ranges, and isolate the acquired data on a per-beat basis for a beat-to-beat analysis.

Although it has been shown that machine learning can be used to diagnose irregular heart rhythms (i.e., arrhythmias) from ECG recordings, which is the standard care used to diagnosed such conditions, the standard for the diagnosis of coronary artery disease often includes invasive angiographic test involving cardiac catheterization. The exemplary system beneficially predicts the presence or absence of coronary artery disease solely using non-invasive measurements of the body's biophysical signals.

Methodology for generating the B2B CNN. To generate the convolutional neural network used for the experiments, a training system was developed and used to evaluate large number of potential architectures and hyperparameters via a random search.

Figure 9:
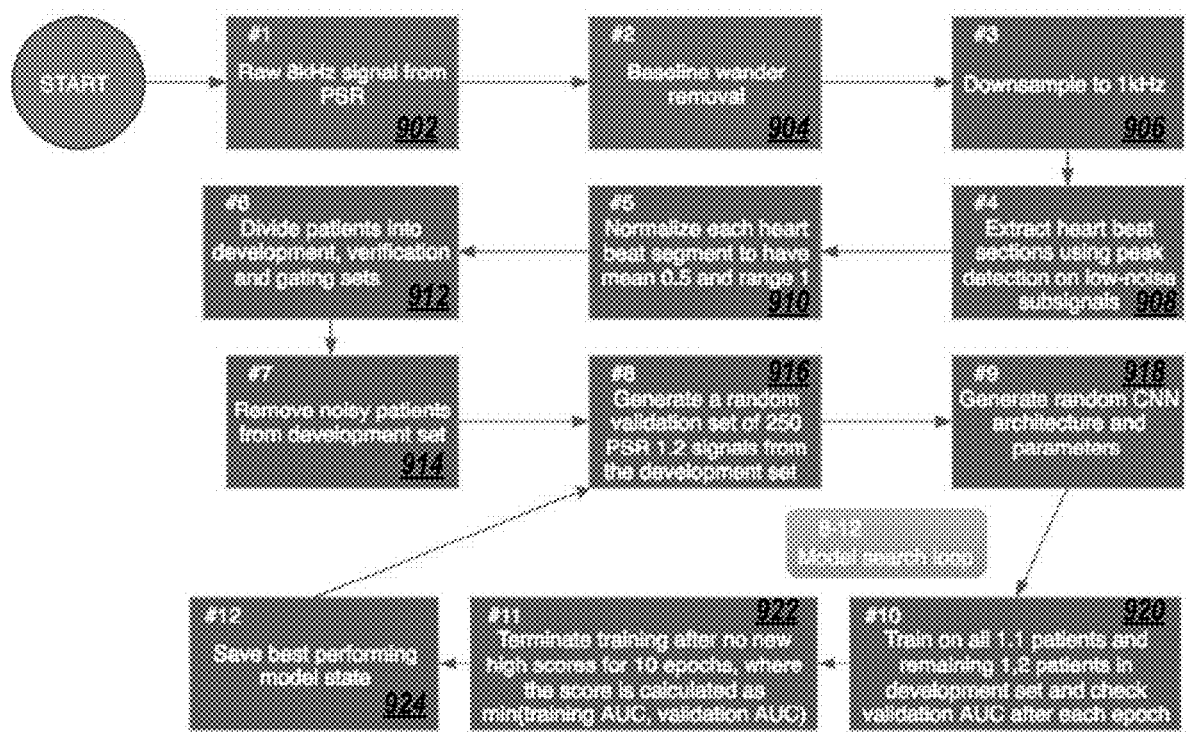
FIG. 9 is a diagram showing a detailed pipeline process to generate one or more neural network model(s) (e.g., one or more deep neural network model(s), one or more convolutional neural network(s) model, etc.) configured to non-invasively assess presence or non-presence of coronary artery disease or a condition in a person, in accordance with an illustrative embodiment.

FIG. 9 is a diagram showing a detailed pipeline process to generate one or more convolutional neural network model(s) configured to non-invasively assess presence or non-presence of coronary artery disease in a person, in accordance with an illustrative embodiment.

In an experiment as shown in FIG. 9, the system in this configuration retrieved at step 902 a patient's raw phase signal data from the acquisition measurement device (e.g., a phase signal recorder or PSR) at 8 kHz. The system removed at step 904 the undesired baseline signal from the acquired raw signal to generate a centered data set. The system used a second-order forward-reverse filter configured not to introduce any phase distortion; i.e., no phase response. The filter was configured with an effective high-pass frequency cutoff of 0.8 Hz. Separately, the system evaluated the acquired signal for signal quality and rejected any acquired signals from subsequent analysis failing this test.

The system then downsampled, at step 906, the centered data set from the acquired sampling rate of 8 KHz to 1 KHz using averaging operator to generate a down-sampled centered data set.

After downsampling operation 906, the system extracted at step 908 a set of heart-beat segment data, each comprising a single isolated complete cardiac cycle, from the down-sampled centered data set. The system used the Pan-Tompkins algorithm as described in Pan et al., "A Real-Time QRS Detection Algorithm," IEEE Tran. Biomed. Eng., Vol. 32, No. 3 (March 1985) to detect peaks and to isolate each complete cardiac cycle for each of the acquired channels. The output was in this experiment a fixed window data set of about 0.75-seconds that was centered at a point of highest amplitude and that encompasses a complete cardiac cycle to provide alignment among all of the heart-beat segment data sets. The same process was used to extract sets of cardiac cycle data from each of the acquired channels. During the experiment, because of observed cycle variability noise observed in one of the three acquired channels, only data acquired from two of the measurement channels were used in the analysis (namely, data from channels ORTH1 and ORTH3), although in other embodiments data from all three measurement channels or any two or one channel may be used in the analysis.

The system then normalized at step 910 the value range of each of the extracted heat beat data sets. The system normalized each heart-beat segment data for each of the channels by dividing the data set by a determined maximum absolute value of the data for a given window, thereby bounding the data between a range of −1 and +1. The system then reduced the scale to +0.5 and −0.5 and added an offset of 0.5 to adjust the range to 0.0 and 1.0. As a result, in this experiment, each heart-beat segment data set for each of the channel channels had a mean of 0.5 and a range between 0.0 and 1.0. With the normalization and alignment operation, the input of a given CNN received a similar range and mean for all the training data sets, producing a stronger classifier. Normalizing also makes the signal unitless.

The acquired data set from the CADLAD study were divided at step 912 in this experiment into a development pool, a validation pool, and a gating pool in which the development pool and validation pool were used for training and initial validation and the validation pool and gating pool were used for verification and gating.

The system used, for training and validation, data sets from 730 patients acquired using a first generation phase space recorder (versions 1.0 and 1.1) configured with unipolar wide-band phase-gradient voltage capture for training and validation and from 334 patients acquired using a second generation phase space recorder (version 1.2) configured with bipolar wide-band phase-gradient voltage capture. It was observed that using data sets from different acquisition systems improves the performance of the predictors as compared to using data sets from a single hardware type. The system selected evaluated CNN models having a AUC≥0.57. The system also used a second verification data set that included data from 164 patients acquired using a second generation phase space recorder (version 1.2). The system also used a third gating data set that included data from 243 patients acquired using the second generation phase space recorder (version 1.2).

The experiments were performed using Python3. Packages used included NumPy, Pandas, SciKit-Learn, and Keras, and TensorFlow was used for the backend analysis for the neural networks. All development and experiments were conducted on Amazon Web Services (AWS) servers.

At step 914, the system rejected acquired biophysical-signal data sets having excessive powerline interference noise, excessive high-frequency noise, and excessive cycle variability noise from use as a training, verification, or gating data set. Once all of these pre-processing steps were complete, the model search loop commenced. This loop may be run indefinitely, across multiple machines simultaneously without synchronization. A typical run on 4 p2.xlarge AWS servers would take place in the experiment for 60 hours, which was found to be enough to generate models that meet the validation AUC of 0.6.

The system generated at step 916, for each run through the model search loop, a random validation set of 250 signals from the development set. Stratified sampling was used to have the same ratio of CAD-positive data sets and CAD-negative data sets in both the training and validation sets using the StratifiedShuffleSplit function in SciKit-Learn package, which is described in http://scikit-learn.org/stable/modules/generated/sklearn.model_selection.StratifidShuffleSplit.html and which is incorporated by reference herein in its entirety. The remaining data set in the development set that was not used in the validation set was used for training (814 in total).

At step 918, the system randomly generated a set of hyperparameters for a CNN architecture from a search space as provided in Table 1. These hyperparameters were specific to the experimental work and were found to cover the ranges of interest for all the parameters in the experiments studied. The system used Keras open-source neural network library (example code shown in FIG. 6) to construct CNN models from the hyperparameter search space.

The system trained, at step 920, the CNN model over several epochs in which each epoch includes a single pass through of the entire training set. At the end of each epoch, the system in the experiment calculated the training and validation AUCs. The system calculated the score of that epoch as the minimum of the AUCs of the current version of the model for the training and validation signals but using an observed worst-case rather than best-case scenario for the selection of the CNN model.

At step 922, the system terminated training after 10 epochs in which no new high score is observed.

At each run, the system saved at step 924 a best scoring model along with the corresponding hyperparameters and corresponding predictions on the verification data set.

Figure 10:
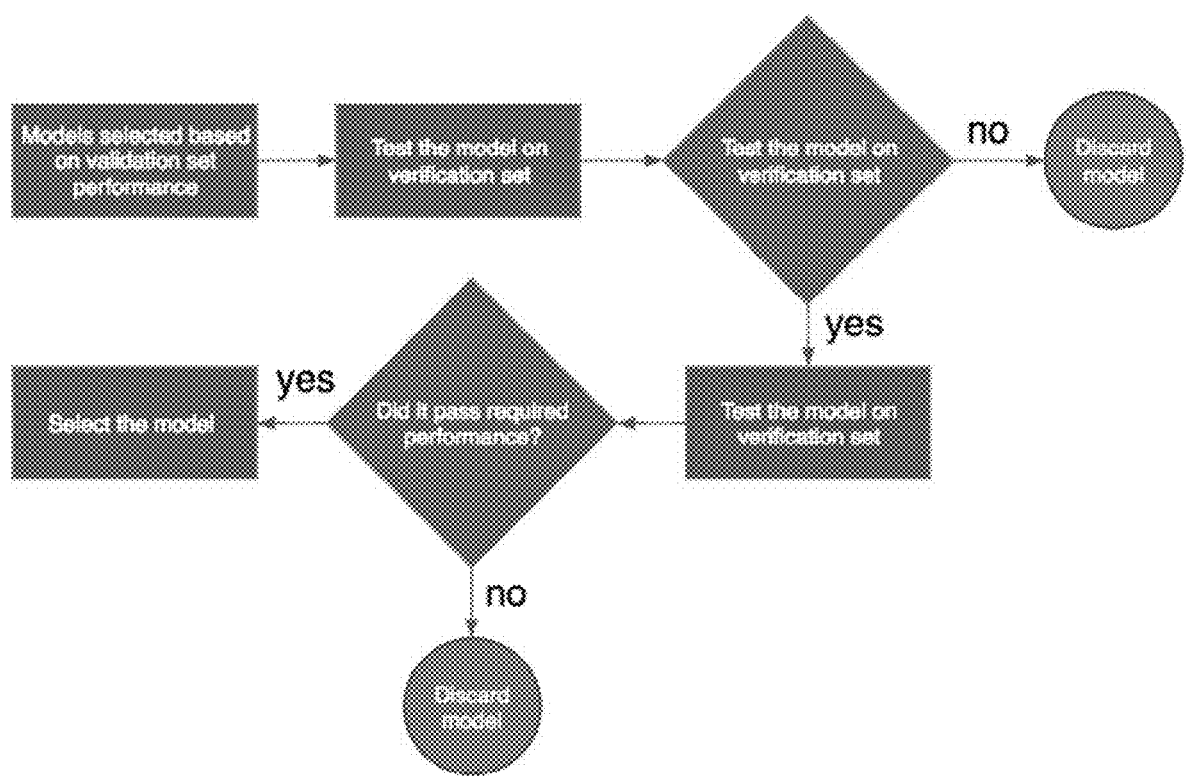
FIG. 10 is a diagram showing a process to select a neural network model (e.g., a deep neural network model, a convolutional neural network model, etc.) configured to non-invasively assess presence or non-presence of coronary artery disease or a condition in a person, in accordance with an illustrative embodiment.

FIG. 10 is a diagram showing a process to select a convolutional neural network model configured to non-invasively assess presence or non-presence of coronary artery disease in a person, in accordance with an illustrative embodiment.

Top scoring models, e.g., those having AUCs of 0.58 or greater separately on men and on women in the validation set were selected in the experiment from the model search to be tested on the verification set. Those models that had AUCs≥0.57 on the verification set were selected to have their performance further evaluated on the larger gating set. These AUCs were chosen as the thresholds, as they were found to be the optimum values to allow the generation of the required number of predictive models that had different characteristics. All models selected to be tested on the gating set were tested simultaneously to avoid biasing the model selection process. Bootstrap Confidence Intervals (CIs) were calculated in the experiment on the verification and gating set performances using the Matlab R2016b function bootci as well.

Training Labels for B2B CNN. The system used in the experiment training labels that derived using a Gensini-based score (which assigns a score to a data set that reflects the total burden on the myocardium as caused by a subject's coronary lesions localized and quantified by coronary angiography).

This score defined by Gensini includes a severity weight and a location weight. According to the severity weighting, a coronary lesion is assigned a value of 1, 2, 4, 8, 16, and 32 (exponential scale) according to a respective diameter reduction of 25%, 50%, 75%, 90%, 99% and 100%. According to the location weighting, a coronary lesion is assigned a score between 0.5 and 5 that reflect the relative impact on the overall myocardium according to its location. For example, if the lesion is upstream in the coronary circulation (e.g., proximal to the aorta), then that lesion affects circulation to a greater degree of myocardial territory than a lesion that is further downstream (distal) in the circulation. A location that most impacts the circulation was assigned a value of 5, and a location that least impact circulation was assigned a value of 0.5.

Two Gensini-based scorings were evaluated. The first Gensini-based scoring used a summation of all of the weighted score as the training label for a given data. The second Gensini-based scoring used only the worst-case lesion; i.e., the lesion with the maximal value of severity multiplied by location. It was observed that the second modified Gensini score is more tractable for machine learning models. Further, the system applied a logarithm operation to the modified Gensini score to change the exponential distribution to a linear distribution, making the label more tractable for machine learning models.

Results of B2B CNN Experiment. Experimental results of the performance of the CNN are presented in Tables 3 and 4 (evaluated using the gating data set), Table 5 (evaluated using the verification data set), and Table 6 (using the combined verification and gating data sets).

Tables 3 and 4 show performance scores evaluated for two models from a gating data set of N=213 subjects using an 85% threshold (in which 92 are women, of which 14 are diagnosed with CAD, and in which 121 are men, of which 55 are diagnosed with CAD). Bootstrap confidence intervals ("CI") are shown in parentheses. Thresholds were determined based on the desired performance on the verification set, i.e., specificity≥0.65, sensitivity as high as possible. Two models (referred to as "Model 85" and "Model 129") were observed to satisfy the selection criteria.

TABLE 3

| Model | AUC | Sensitivity | Specificity | AUC-men only | AUC-women only |
|---|---|---|---|---|---|
| 85 | 0.57 (0.48, 0.65) | 0.39 (0.28, 0.51) | 0.69 (0.61, 0.76) | 0.50 (0.40, 0.60) | 0.59 (0.43, 0.77) |

TABLE 4

| Model | AUC | Sensitivity | Specificity | AUC-men only | AUC-women only |
|---|---|---|---|---|---|
| 129 | 0.59 (0.50, 0.67) | 0.46 (0.34, 0.58) | 0.67 (0.60, 0.75) | 0.51 (0.40, 0.61) | 0.55 (0.40, 0.70) |

Table 5 shows performance scores for the two models evaluated from a verification set of N=130 using the 85% noise thresholds (in which 58 are women, of which 12 are diagnosed with CAD, and in which 72 are men, of which 35 are diagnosed with CAD). Thresholds were determined based on desired performance on this set, i.e., specificity≥0.65, sensitivity as high as possible. Bootstrap CIs are shown in parentheses. As shown, all of these models had AUC scores in the range of 0.62 and 0.65.

TABLE 5

| Model | AUC | Sensitivity | Specificity | AUC-men only | AUC-women only |
|---|---|---|---|---|---|
| 85 | 0.55 (0.44, 0.65) | 0.45 (0.30, 0.59) | 0.65 (0.54, 0.75) | 0.53 (0.39, 0.66) | 0.43 (0.22, 0.63) |
| 129 | 0.61 (0.51, 0.71) | 0.49 (0.35, 0.64) | 0.71 (0.60, 0.80) | 0.59 (0.44, 0.71) | 0.49 (0.29, 0.68) |

Table 6 shows performance scores for the two models evaluated from a combined verification and gating data set of N=343 using the 85% noise thresholds (in which 150 are women, of which 26 have CAD and in which 193 are mend, of which 90 have CAD. Thresholds were determined based on desired performance on this set, i.e., specificity≥0.65, sensitivity as high as possible. Bootstrap CIs are shown in parentheses. As shown in Tables 3 and 4, both models have AUC scores in the range if 0.62 and 0.65.

TABLE 6

| Model | AUC | Sensitivity | Specificity | AUC-men only | AUC-women only |
|---|---|---|---|---|---|
| 85 | 0.57 (0.50, 0.63) | 0.41 (0.33, 0.5) | 0.65 (0.59, 0.71) | 0.51 (0.43, 0.59) | 0.52 (0.39, 0.64) |
| 129 | 0.60 (0.53, 0.66) | 0.49 (0.40, 0.58) | 0.66 (0.60, 0.72) | 0.54 (0.45, 0.62) | 0.52 (0.41, 0.65) |

B2B CNN Model. As noted above, two CNN models (referred to as "Model 85" and "Model 129") were observed to satisfy the selection criteria on the validation set. Table 7 shows hyperparameters of the two CNN models.

TABLE 7

| Parameter | Model "85" | Model "129" |
|---|---|---|
| batch size | 64 | 512 |
| learning rate | 0.000797880786504141 | 0.0002666236070084216 |
| # convolutional layers | 4 | 2 |
| filter size | 38 | 10 |
| # filters in first convolutional layer | 2 | 4 |
| increase in # filters in subsequent layers | 'x2' | 'x2' |
| # additional dense layers | 0 | 0 |
| size of additional dense layers | NA | NA |
| activation function | 'softsign' | 'elu' |
| target | 'log max gensini' | 'log max gensini' |
| input frequency | 1000 Hz | 250 Hz |
| dilation rate | 3 | 3 |
| size of max pooling | 27 | 9 |
| dropout | 0.5 | 0.5 |
| final layer activation function | 'sigmoid' | 'sigmoid' |
| loss function | 'mean_squared_logarithmic_error' | 'mean_squared_logarithmic_error' |
| optimizer | 'Adam' | 'Adam' |

Localization Convolutional Neural Network. Experiments were conducted from the data acquired from the CADLAD study to show that the exemplary system can detect location of significant coronary artery disease (CAD) in a subject's specific coronary artery via a convolutional neural network (CNN) that is trained with wide-band phase-gradient biopotential signal data sets. Similar to a B2B CNN model, the wide-band phase-gradient voltage data are only pre-processed to remove baseline wander, normalize the data ranges, and isolate the acquired data on a per-beat basis for a beat-to-beat analysis. The experiments were conducted for three coronary arteries, namely, the left anterior descending artery (LAD), the left circumflex artery (LCX), and the right coronary artery (RCA).

Methodology for generating the localization CNN. To generate the convolutional neural network used for the experiments, a training system was developed and used to evaluate large number of potential architectures and hyperparameters via a random search. FIG. 9 shows a process for the complete model-generating pipeline.

As described above, and as shown in FIG. 9, the system (e.g., as described in reference to embodiment 110, 110a, 110b) retrieved raw collected patient's phase signal from the acquisition measurement device or a repository. The system removed undesired baseline signal from the acquired raw signal to generate a centered data set. The system used a second-order forward-reverse filter configured not to introduce any phase distortion; i.e., no phase response. The filter was configured with an effective high-pass frequency cutoff of 0.8 Hz. Separately, the system evaluated the acquired signal for signal quality and rejected any acquired signals from subsequent analysis failing this test.

As described above, the system then downsampled from centered data set from the acquired sampling rate of 8 KHz to 1 KHz using an averaging operator to generate a down-sampled centered data set.

As described above, after the downsampling operation, the system extracted a set of heart-beat segment data set each comprising a single isolated complete cardiac cycle from the down-sampled centered data set. The system used the Pan-Tompkins algorithm to detect peaks and to isolate each complete cardiac cycle for each of the acquired channels. The output is a fixed window data set of about 0.75-second that is centered at a point of highest amplitude and that encompasses a complete cardiac cycle to provide alignment among all of the heart-beat segment data sets. The same process is used to extract sets of cardiac cycle from each of the acquired channels. During the experiments, because of observed cycle variability noise observed in one of the three acquired channels, only data acquired from two of the measurement channels were used in the analysis (namely, data from channels ORTH1 and ORTH3).

As described above, the system then normalized the value range of each of the extracted heat beat. The system normalized each heart-beat segment data for each of the channels by dividing the data set by a determined maximum absolute value of the data for a given window, thereby bounding the data between a range of −1 and +1. The system then reduced the scale to +0.5 and −0.5 and added an offset of 0.5 to adjust the range to 0.0 and 1.0. As a result, each heart-beat segment data set for each of the channel channels had a mean of 0.5 and a range between 0.0 and 1.0. With the normalization and alignment operation, the input of a given CNN received a similar range and mean for all the training data set, producing a stronger classifier. Normalizing also makes the signal unitless. The acquired data set from the CADLAD study were divided into a development pool and validation pool.

The system used, for training and validation, data sets from 730 patients acquired using a first generation phase space recorder (version 1.0 and 1.1) configured with unipolar wide-band phase-gradient voltage capture for training and validation and from 334 patients acquired using a second generation phase space recorder (version 1.2) configured with bipolar wide-band phase-gradient voltage capture. It was observed that using data sets from different acquisition systems improves the performance of the predictors as compared to using data set from a single hardware type. The system selected evaluated CNN models having a AUC≥0.57. The system also used a second verification data set that includes data from 164 patients acquired using the second generation phase space recorder (version 1.2). The system also used a third gating data set that includes data from 243 patients acquired using the second generation phase space recorder (version 1.2)

The system generated a set of hyperparameters for a CNN architecture from a search space as provided in Table 8. The system used a modified version of the Keras code shown in FIG. 6 to construct CNN models from the hyperparameter search space. The system trained the CNN model over several epochs in which each epoch includes a single pass through of the entire training set. At the end of each epoch, the system calculated the training and validation AUCs. The system calculated the score of that epoch as the minimum of the AUCs of the current version of the model for the training and validation signals but using an observed worst-case rather than best-case scenario for the selection of the CNN model. The system terminated a run after 10 epochs in which no new high score is observed. At each run, the system saved a best scoring model along with the corresponding hyperparameters and corresponding predictions on the verification data set.

TABLE 8

| Parameter | Localization Model |
|---|---|
| batch size | 1024 |
| learning rate | 0.000272669120574 |
| # convolutional layers | 4 |
| first convolutional layer filter size | 17 |
| # filters in first convolutional layer | 14 |
| stride | 1 |
| # additional dense layers | 1 |
| size of additional dense layers | 10 |
| activation function | 'tanh' |
| target | ['LAD', 'LCX', 'RCA] |
| input frequency | 1000 Hz |
| size of max pooling | 1 |
| dropout | 0.224455889694 |
| loss function | 'mean_squared_error' |
| optimizer | 'Adam' |
| input channels | [ORTH1, ORTH2] |

Because at least one positive prediction from the CAD model was needed to have a positive prediction of the localization model, the system was configured to trigger the prediction from the localization model when a positive prediction is determined from the CAD model.

Training Labels for localization CNN. Once the system determined sets of candidate hyperparameters, the system trained the neural networks on training sets to learn binary labels of LAD, LCX, and RCA (e.g., "0" refers to no disease and "1" refers to disease). The labels were obtained and assessed from angiography reports of the patients per the CADLAD study protocol. For the study, the target was a vector of length three with binary values of LAD, LCX, and RCA. For instance, target [1, 0, 1] indicates that LAD label is 1, LCX label is 0, and RCA label is 1. Therefore, the predictions of the models were also in the form of a vector of length three, with predictions for LAD, LCX, and RCA, respectively.

Results of localization CNN experiment. Table 9 shows experimental results of the performance of the localization CNN evaluated using the gating and verification data set. Table 9 shows the results for the localization model for a test set of N=411 subjects, of which 101 were diagnosed with CAD in the LAD, 66 were diagnosed with CAD in the LCX, and 72 were diagnosed with CAD in the RCA. The results provide both the statistics for the overall case in which all three arteries predictions are combined and also the statistics for each of the individual arteries. The system calculated the thresholds such that for each case, the sensitivity and specificity (when all three predictions are combined in one set) would be maximized over a value of 75% sensitivity and 65% specificity, resulting in threshold values of about −0.01169, about −0.0311, and about 0.0178 for the LAD, LCX, and RCA predictions, respectively. This method resulted in positive predictions for almost all the arteries for the cases when CAD was predicted positive.

TABLE 9

| Model | AUC | Sensitivity | Specificity |
|---|---|---|---|
| Overall | 0.67 (0.64, 0.70) | 0.74 (0.68, 0.79) | 0.60 (0.57, 0.63) |
| LAD | 0.69 (0.64, 0.75) | 0.76 (0.66, 0.84) | 0.63 (0.57, 0.69) |
| LCX | 0.67 (0.61, 0.72) | 0.76 (0.63, 0.85) | 0.58 (0.53, 0.64) |
| RCA | 0.67 (0.61, 0.73) | 0.72 (0.61, 0.82) | 0.61 (0.56, 0.66) |

To avoid or minimize the likelihood of over-prediction of positives for arteries, the system was configured to choose a threshold having a value of 0.1116, 0.1596, and 0.1840, respectively, to provide 72% CAD positive for LAD, 45% CAD positive for LCX, and 53% CAD positive for RCA, respectively. In other words, for LAD, this threshold resulted in a positive prediction for 72% of the instances of a subject being CAD positive in the LCAD; 45% of the instances of a subject being CAD positive in the LCX; and 53% of the instances of a subject being CAD positive in the RCA.

Table 10 shows the results for overall and individual arteries for all the patients in the test set (N=411 patients, of which 101 were diagnosed with CAD in the LAD, 66 were diagnosed with CAD in the LCX, and 72 were diagnosed with CAD in the RCA).

TABLE 10

| Model | AUC | Sensitivity | Specificity |
|---|---|---|---|
| Overall | 0.62 (0.58, 0.65) | 0.45 (0.39, 0.51) | 0.78 (0.75, 0.81) |
| LAD | 0.65 (0.59, 0.70) | 0.55 (0.46, 0.64) | 0.74 (0.68, 0.78) |
| LCX | 0.58 (0.53, 0.65) | 0.35 (0.27, 0.48) | 0.82 (0.77, 0.85) |
| RCA | 0.59 (0.53, 0.65) | 0.39 (0.29, 0.51) | 0.78 (0.74, 0.83) |

Discussion for localization CNN. The localization CNN study showed that women, at least those observed in the CADLAD study, tend to have CAD in single arteries. Also, women, at least those observed in the CADLAD study, often develop CAD in the small arteries. These observation likely show that it is harder to detect CAD in women; thus makes women under-diagnosed even during angiography. These results further suggest that to properly diagnose CAD in women, larger and more diversified datasets with higher proportions of diseased women should be used.

Additional experiment data and methodologies, including visual feature analysis, as well additional detail of the methodologies described herein, as performed in the CAD-LAD study, are provided in U.S. Provisional Application No. 62/907,141, which is incorporated herein.

Further, example integration of the B2B CNN and/or localization CNN as described herein to generate a predictive score for presence of disease, including coronary artery disease, is provided in U.S. Provisional Application No. 62/907,141. Further, the B2B CNN and/or localization CNN as described herein, can be used solely, or in combination with other methodologies to characterize LHF, abnormal LVEDP, among other pathologies.

Discussion

The neural network models, for example, deep neural network models such as convolutional neural network models, as described herein, have predictive capability across test sets (i.e., validation sets, verification sets, and gating sets), and can be used in combination with other predictive algorithms to further boost the performance of the convolutional neural network models. The convolutional neural network model search method as described herein can produce algorithms with AUCs of 0.65 or greater. Larger validation sets may provide a better measure of the model's true performance across larger population sets. For example, having a larger data set may provide more examples of each disease distribution, i.e., LAD only, LCX only, RCA only, LAD/LCX, LAD/RCA, LCX/RCA, and LAD/LCX/RCA. These categories could have different disease indications—and thus a larger data set may provide more training examples for the study of each of the categories more rigorously.

Example Computing Environment

Figure 11:
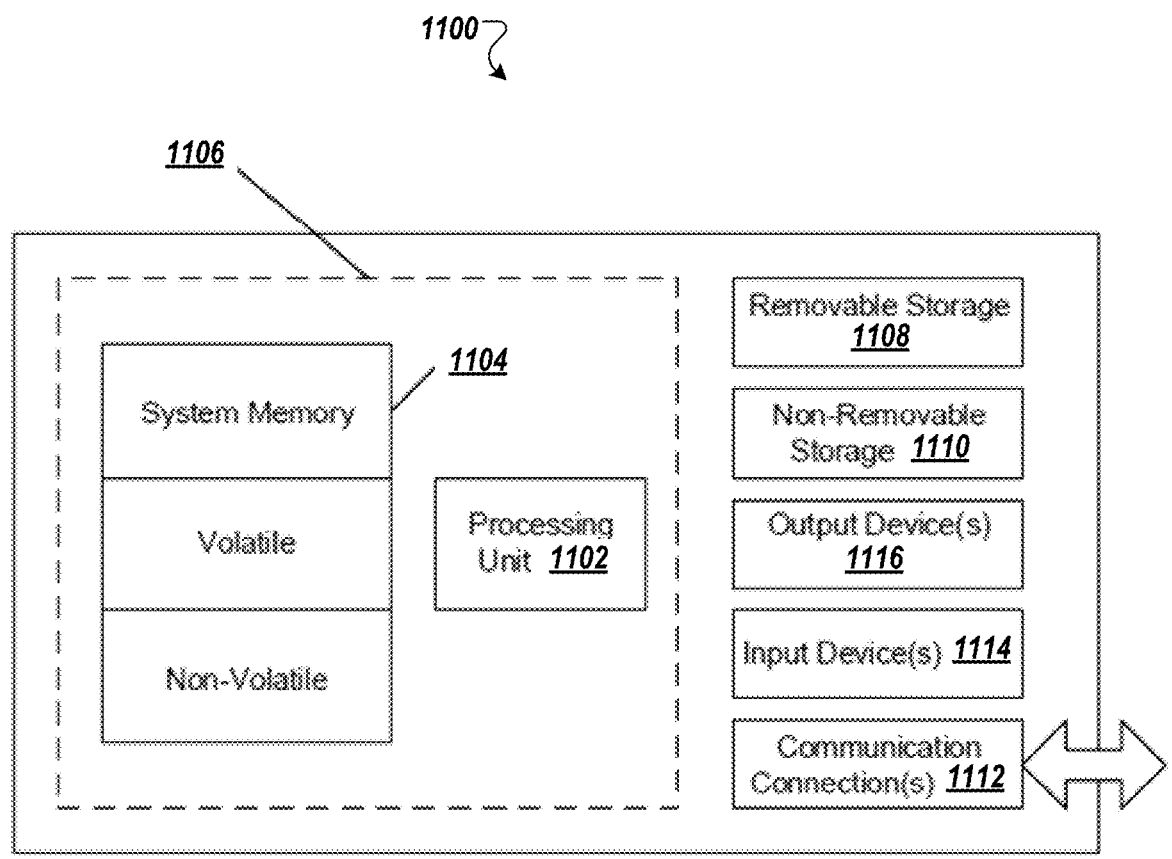
FIG. 11 shows an exemplary computing environment in which example embodiments and aspects may be implemented.

FIG. 11 shows an exemplary computing environment in which example embodiments and aspects may be implemented.

The computing device environment is only one example of a suitable computing environment and is not intended to suggest any limitation as to the scope of use or functionality.

Numerous other general-purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 11, an exemplary system for implementing aspects described herein includes a computing device, such as computing device 1100. In its most basic configuration, computing device 1100 typically includes at least one processing unit 1102 and memory 1104. Depending on the exact configuration and type of computing device, memory 1104 may be volatile (such as random access memory (RAM)), non-volatile (such as read-only memory (ROM), flash memory, etc.), or some combination of the two. This most basic configuration is illustrated in FIG. 11 by dashed line 1106.

Computing device 1100 may have additional features/functionality. For example, computing device 1100 may include additional storage (removable and/or non-removable) including, but not limited to, magnetic or optical disks or tape. Such additional storage is illustrated in FIG. 11 by removable storage 1108 and non-removable storage 1110.

Computing device 1100 typically includes a variety of computer readable media. Computer readable media can be any available media that can be accessed by the device 1100 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 1104, removable storage 1108, and non-removable storage 1110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by computing device 1100. Any such computer storage media may be part of computing device 1100.

Computing device 1100 may contain communication connection(s) 1112 that allow the device to communicate with other devices. Computing device 1100 may also have input device(s) 1114 such as a keyboard, mouse, pen, voice input device, touch input device, etc, singularly or in combination. Output device(s) 1116 such as a display, speakers, printer, vibratory mechanisms, etc. may also be included singularly or in combination. All these devices are well known in the art and need not be discussed at length here.

It should be understood that the various techniques described herein may be implemented in connection with hardware components or software components or, where appropriate, with a combination of both. Illustrative types of hardware components that can be used include Graphical Processing Units (GPUs), Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, handheld devices, and wearable devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Further examples of processing that may be used with the exemplified method and system are described in: U.S. Pat. No. 9,289,150, entitled "Non-invasive Method and System for Characterizing Cardiovascular Systems"; U.S. Pat. No. 9,655,536, entitled "Non-invasive Method and System for Characterizing Cardiovascular Systems"; U.S. Pat. No. 9,968,275, entitled "Non-invasive Method and System for Characterizing Cardiovascular Systems"; U.S. Pat. No. 8,923,958, entitled "System and Method for Evaluating an Electrophysiological Signal"; U.S. Pat. No. 9,408,543, entitled "Non-invasive Method and System for Characterizing Cardiovascular Systems and All-Cause Mortality and Sudden Cardiac Death Risk"; U.S. Pat. No. 9,955,883, entitled "Non-invasive Method and System for Characterizing Cardiovascular Systems and All-Cause Mortality and Sudden Cardiac Death Risk"; U.S. Pat. No. 9,737,229, entitled "Noninvasive Electrocardiographic Method for Estimating Mammalian Cardiac Chamber Size and Mechanical Function"; U.S. Pat. No. 10,039,468, entitled "Noninvasive Electrocardiographic Method for Estimating Mammalian Cardiac Chamber Size and Mechanical Function"; U.S. Pat. No. 9,597,021, entitled "Noninvasive Method for Estimating Glucose, Glycosylated Hemoglobin and Other Blood Constituents"; U.S. Pat. No. 9,968,265, entitled "Method and System for Characterizing Cardiovascular Systems From Single Channel Data"; U.S. Pat. No. 9,910,964, entitled "Methods and Systems Using Mathematical Analysis and Machine Learning to Diagnose Disease"; U.S. Patent Publication No. 2017/0119272, entitled "Method and Apparatus for Wide-Band Phase Gradient Signal Acquisition"; PCT Publication No. WO2017/033164, entitled "Method and Apparatus for Wide-Band Phase Gradient Signal Acquisition"; U.S. Patent Publication No. 2018/0000371, entitled "Non-invasive Method and System for Measuring Myocardial Ischemia, Stenosis Identification, Localization and Fractional Flow Reserve Estimation"; PCT Publication No. WO2017/221221, entitled "Non-invasive Method and System for Measuring Myocardial Ischemia, Stenosis Identification, Localization and Fractional Flow Reserve Estimation"; U.S. Pat. No. 10,292,596, entitled "Method and System for Visualization of Heart Tissue at Risk"; U.S. patent application Ser. No. 16/402,616, entitled "Method and System for Visualization of Heart Tissue at Risk"; U.S. Patent Publication No. 2018/0249960, entitled "Method and System for Wide-band Phase Gradient Signal Acquisition"; U.S. patent application Ser. No. 16/232,801, entitled "Method and System to Assess Disease Using Phase Space Volumetric Objects"; PCT Application No. IB/2018/060708, entitled "Method and System to Assess Disease Using Phase Space Volumetric Objects"; U.S. Patent Publication No. US2019/0117164, entitled "Methods and Systems of De-Noising Magnetic-Field Based Sensor Data of Electrophysiological Signals"; U.S. Publication No. 2019/0214137, filed on Dec. 26, 2018, entitled "Method and System to Assess Disease Using Phase Space Tomography and Machine Learning"; PCT Application No. PCT/IB2018/060709, entitled "Method and System to Assess Disease Using Phase Space Tomography and Machine Learning"; U.S. Publication No. 2019/0384757, entitled "Methods and Systems to Quantify and Remove Asynchronous Noise in Biophysical Signals," filed Jun. 18, 2019; U.S. patent application Ser. No. 16/725,402, concurrently filed herewith, entitled "Method and System to Assess Disease Using Phase Space Tomography and Machine Learning" claiming priority to U.S. Patent Provisional Application Nos. 62/784,984 and 62/835,869; U.S. Publication No. 2019/0365265, entitled "Method and System to Assess Pulmonary Hypertension Using Phase Space Tomography and Machine Learning"; U.S. patent application Ser. No. 16/725,416, concurrently filed herewith, entitled "Method and System for Automated Quantification of Signal Quality" and claiming priority to U.S. Patent Provisional Application No. 62/784,962; U.S. patent application Ser. No. 15/653,433, entitled "Discovering Novel Features to Use in Machine Learning Techniques, such as Machine Learning Techniques for Diagnosing Medical Conditions"; U.S. patent application Ser. No. 15/653,431, entitled "Discovering Genomes to Use in Machine Learning Techniques"; U.S. application Ser. No. 16/831,264, entitled "Method and System to Assess Disease Using Dynamic Analysis of Biophysical Signals" claiming priority to U.S. Patent Provisional Application No. 62/862,991; U.S. application Ser. No. 16/831,380, entitled "Method and System to Assess Disease Using Dynamical Analysis of Cardiac and Photoplethysmographic Signals" claiming priority to U.S. Patent Provisional Application No. 62/863,005, each of which is incorporated by reference herein in its entirety.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; the number or type of embodiments described in the specification.

While the methods and systems have been described in connection with certain embodiments and specific examples, it is not intended that the scope be limited to the particular embodiments set forth, as the embodiments herein are intended in all respects to be illustrative rather than restrictive.

The methods, systems and processes described herein may be used generate stenosis and FFR outputs for use in connection with procedures such as the placement of vascular stents within a vessel such as an artery of a living (e.g., human) subject, and other interventional and surgical system or processes. In one embodiment, the methods, systems and processes described herein can be configured to use the FFR/stenosis outputs to determine and/or modify, intra operation, a number of stents to be placed in a living (e.g., human), including their optimal location of deployment within a given vessel, among others.

Examples of other biophysical signals that may be analyzed in whole, or in part, using the exemplary methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The exemplary analysis can be used in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

When any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A method comprising:
receiving, by a processor, a biophysical signal data set of a subject acquired from two or more channels of one or more sensors, including a first channel and a second channel;
pre-processing the biophysical signal data set to generate one or more pre-processed data sets, wherein the pre-processed data set of the first channel includes a plurality of singularly isolated complete phase synchronized cardiac cycles, each isolated complete phase synchronized cardiac cycle having a signal peak and a same time window correspondence at boundaries of an isolated complete phase synchronized cardiac cycle to another singularly isolated complete phase synchronized cardiac cycle of the second channel; and
determining, by the processor, a value indicative of presence or non-presence of heart failure by directly inputting the pre-processed data set to one or more deep neural networks trained with a set of training biophysical signal data acquired from patients diagnosed with the heart failure and labeled with the presence or non-presence of the heart failure,
wherein an output data set is outputted via a report and/or a display based on the determined value indicative of the presence or non-presence of heart failure.

2. The method of claim 1, wherein the step of pre-processing the biophysical signal data set comprises:
segmenting, by the processor, a portion of the biophysical signal data set, or a normalized data set derived from the portion of the biophysical signal data set, associated with a first channel of the two or more channels, into one or more first segmented data sets, wherein each of the first segmented data sets includes a single isolated complete cardiac cycle as a first single isolated completed cardiac cycle, wherein the first single isolated complete cardiac cycle has an associated time window; and
segmenting, by the processor, another portion of the biophysical signal data set, or a normalized data set derived from the another portion of the biophysical signal data set, the another portion of the biophysical signal data set associated with a second channel of the one or more channels, into one or more second segmented data sets, wherein each of the one or more second segmented data sets includes a second single isolated complete cardiac cycle and, wherein the second single isolated complete cardiac cycle has an associated time window corresponding to that of the first single isolated complete cardiac cycle to provide phase synchronized data sets.

3. The method of claim 1, further comprising:
comparing, by the processor, the value indicative of the presence or non-presence of heart failure to a threshold value,
wherein the step of determining the presence or non-presence of heart failure is performed based on the comparison.

4. The method of claim 1, wherein the step of pre-processing the biophysical signal data set to generate one or more pre-processed data sets further comprises a second pre-processing operation selected from the group consisting of:
performing a down-sampling operation;
performing a baseline wander removal operation; and
performing a normalization operation.

5. The method of claim 1, wherein at least one of the one or more deep neural networks is configured based on a hyperparameter search loop operation, wherein the hyperparameter search loop operation comprises:

generating, by the processor, a plurality of hyperparameter sets for a template convolutional neural network, wherein each of the plurality of hyperparameter sets is generated by a random or pseudo-random selection from a set of candidate hyperparameters, wherein at least one hyperparameter of the set of candidate hyperparameters is selected from a group consisting of: batch size, learning rate, convolutional layer, filter size, a number of filter in a first convolutional layer, an increase in filter in subsequent layer, number of additional dense layers, size of additional dense layers, activation function type, target, dilation rate, and dropout;

training, by the processor, for each of a plurality of hyperparameter sets, the template convolutional neural network, wherein in each instance of an evaluation, the template convolutional neural network is configured with a hyperparameter set of the plurality of hyperparameter sets; and evaluating, by the processor, for each of the plurality of hyperparameter sets, the trained deep neural network with a first validation data set, wherein each evaluation generates a score.

6. The method of claim 5, wherein the at least one of the one or more deep neural networks is configured based on a Bayesian hyperparameter optimization.

7. The method of claim 5, wherein the evaluation of the trained deep neural network includes generating an accuracy score, a weighted accuracy score, a positive predictive score, a negative predictive score, a F-score, a sensitivity score, a specificity score, and/or a diagnostic odds ratio score.

8. The method of claim 1, further comprising:

modifying the value indicative of presence or non-presence of heart failure based on one or more additional predictive models, wherein the one or more additional predictive models involve analysis based on geometric features associated with geometric shape or topology of the biophysical signal data set in phase space.

9. The method of claim 8, wherein the one or more additional predictive models involve analysis based on geometric features associated with geometric shape or topology of the biophysical signal data set in phase space, and wherein the geometric features associated with geometric shape or topology of the biophysical signal data set in phase space includes a quantification of the biophysical signal data set in a region in phase space occupied by identified ventricular depolarization trajectories.

10. The method of claim 1, further comprising:

merging the value indicative of presence or non-presence of heart failure with a second predictive value indicative of presence or non-presence of heart failure, wherein the second predictive value indicative of presence or non-presence of heart failure is based on one or more additional predictive models.

11. The method of claim 1, wherein the pre-processing generates the pre-processed data set that includes fiducial points corresponding to at least one of a machine-identified maximal ventricular depolarization, a machine-identified point prior to the maximal ventricular depolarization, and a machine-identified conclusion of ventricular depolarization.

12. The method of claim 1, wherein the value indicative of presence or non-presence of heart failure is indicative of left-side heart failure.

13. The method of claim 1, wherein the value indicative of presence or non-presence of heart failure is indicative of right-side heart failure.

14. A system comprising:

an acquisition device configured to acquire a biophysical signal data set of a subject acquired from two or more channels of one or more sensors, including a first channel and a second channel; and an assessment system coupled, directly or indirectly, to said device, the assessment system comprising:

one or more processors; and a memory having instructions stored thereon, wherein execution of the instruction by the one or more processors cause the one or more processors to:

receive the biophysical signal data set from the acquisition device;

pre-process the biophysical signal data set to generate one or more pre-processed data sets, wherein the pre-processed data set of the first channel includes a plurality of singularly isolated complete phase synchronized cardiac cycles, each isolated complete phase synchronized cardiac cycle having a signal peak and a same time window correspondence at boundaries of an isolated complete phase synchronized cardiac cycle to another singularly isolated complete phase synchronized cardiac cycle of the second channel; and determine a value indicative of presence or non-presence of heart failure by directly inputting the pre-processed data sets to one or more deep neural networks trained with a set of training biophysical signal data acquired from patients diagnosed with the heart failure and labeled with the presence or non-presence of the heart failure, and wherein an output data set is outputted via a report and/or a display based on the determined value indicative of the presence or non-presence of heart failure.

* * * * *